(12) United States Patent
Zaleski

(10) Patent No.: US 7,181,054 B2
(45) Date of Patent: Feb. 20, 2007

(54) SYSTEM FOR PROCESSING IMAGE REPRESENTATIVE DATA

(75) Inventor: John R. Zaleski, West Brandywine, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 902 days.

(21) Appl. No.: 10/107,229

(22) Filed: Mar. 27, 2002

(65) Prior Publication Data

US 2003/0048932 A1 Mar. 13, 2003

Related U.S. Application Data

(60) Provisional application No. 60/348,602, filed on Jan. 15, 2002, provisional application No. 60/316,602, filed on Aug. 31, 2001.

(51) Int. Cl.
*G06K 9/00* (2006.01)
(52) U.S. Cl. ........................... 382/128
(58) Field of Classification Search ............... 382/103, 382/128
See application file for complete search history.

(56) References Cited

U.S. PATENT DOCUMENTS

| | | | |
|---|---|---|---|
| 3,654,916 A | 4/1972 | Neilson | 128/2.06 |
| 4,197,854 A | 4/1980 | Kasa | 128/630 |
| 4,570,225 A | 2/1986 | Lundy | 364/417 |
| 4,831,526 A | 5/1989 | Luchs et al. | 364/401 |
| 5,191,524 A | 3/1993 | Pincus et al. | 364/413.05 |
| 5,199,439 A | 4/1993 | Zimmerman et al. | 128/670 |
| 5,800,347 A | 9/1998 | Skates et al. | 600/300 |
| 5,819,230 A | 10/1998 | Christie et al. | 705/4 |
| 5,819,741 A | 10/1998 | Karlsson et al. | 128/710 |
| 5,860,917 A | 1/1999 | Comanor et al. | 600/300 |

(Continued)

OTHER PUBLICATIONS

"Method of edit color replacement for use with bitmaps" (IBM Technical Disclosure Bulletin, Feb. 1994.*

(Continued)

*Primary Examiner*—Jingge Wu
*Assistant Examiner*—Tom Y. Lu
(74) *Attorney, Agent, or Firm*—Alexander J. Burke

(57) ABSTRACT

The present invention is directed to a system for converting a graphical trace of acquired patient data into digital data suitable for digital signal processing, which includes the steps of receiving data representative of an image including the graphical trace of acquired patient data; analyzing the received data to identify individual pixels comprising the graphical trace in the image representative data; generating a plurality of pixel representative data elements in a desired data format identifying the relative location of the individual pixels in relation to a reference point; generating the desired data format by identifying the relative location of the individual pixels and identifying at least one of, (a) color of said individual pixels and (b) luminance amplitude of said individual pixels; and storing the generated pixel representative data elements in a file. In addition, the received data may be formatted into a format compatible with a procedure located at a remote destination, wherein the procedure is for processing the data representative of the graphical trace to provide processed data suitable for use in presenting the graphical trace in a displayed image; and communicating the formatted data to the remote destination in response to a user command; and generating the displayed image at the remote destination using the formatted data.

48 Claims, 23 Drawing Sheets

U.S. PATENT DOCUMENTS

| | | | |
|---|---|---|---|
| 5,862,304 A | 1/1999 | Ravdin et al. | 395/22 |
| 5,907,828 A | 5/1999 | Meyer et al. | 705/4 |
| 5,941,820 A | 8/1999 | Zimmerman | 600/300 |
| 5,966,700 A | 10/1999 | Gould et al. | 705/38 |
| 6,004,276 A | 12/1999 | Wright et al. | 600/508 |
| 6,021,345 A | 2/2000 | Karagueuzian et al. | 600/518 |
| 6,030,341 A | 2/2000 | Skates et al. | 600/300 |
| 6,059,724 A | 5/2000 | Campell et al. | 600/300 |
| 6,063,026 A | 5/2000 | Schauss et al. | 600/300 |
| 6,110,109 A | 8/2000 | Hu et al. | 600/300 |
| 6,120,440 A | 9/2000 | Goknar | 600/300 |
| 6,179,782 B1 | 1/2001 | Cuce | 600/481 |
| 6,317,731 B1 | 11/2001 | Luciano | 706/21 |
| 6,330,541 B1 | 12/2001 | Meyer et al. | 705/4 |
| 6,580,817 B2 * | 6/2003 | Badilini | 382/128 |
| 6,956,584 B2 * | 10/2005 | Ishihara | 345/620 |
| 2001/0047326 A1 | 11/2001 | Broadbent et al. | 705/38 |

OTHER PUBLICATIONS http://www.silkscientific.com/usiginfo/body.htm.*
Silkscientific.com http://www.silkscientific.com.
B. Tummers: "DataThief II, version 1.1.0" Internet Article, Online! Nov. 6, 2000 XP002273768 www.nikhef.nl/{keeshu/datathief/> .
M.D. Silbert: "New Graphs from Old" L'Actualite Chimique Canadienne, Mar. 2000 XP002273769.
J.E. Silk, E.M. Woolley: "Converting scanned graphs to (x,y) data" American Laboratory, Online! Feb. 1999 XP002273770 www.iscpubs.com/articles/a1/a9902sil.pdf>.
Anonymous: "Digitizing programs for converting hard copy graphs and plots back to data" Internet Article, Online! Apr. 5, 2003 XP002273771 www.ccp14.ac.uk/solution/hardcopy2data.htm>.
International Search Report.

* cited by examiner

Figure 19

SYSTEM FOR PROCESSING IMAGE REPRESENTATIVE DATA

The present application is a non-provisional application of provisional application having Ser. No. 60/316,602 filed by John R. Zaleski on Aug. 31, 2001 and U.S. Provisional Application Ser. No. 60/348,602, entitled "System for Remote Plotting of a Graphical Trace," filed Jan. 15, 2002.

BACKGROUND OF THE INVENTION

1. Field of the Invention

The present invention is directed to a system for translating hardcopy clinical patient signals into an electronic format that can be analyzed by a computer, stored, and later displayed in graphical form remotely over a computer network. More particularly, the present invention is directed to a software application that enables hardcopy Electroencephalogram (EEG) and Electrocardiogram (ECG) charts to be converted into an electronic format that can be received, analyzed, and stored by a Web server, and then transmitted to a Web browser upon request.

2. Description of the Prior Art

In a typical primary care physician's office (or even in some acute care units at hospitals) ECG tests are performed on patients. These tests are typically performed using the standard 3- or 12-lead methods in which a pen records the time-varying ECG signal on a paper strip. These devices are sometimes called "paper strip recorders."

The paper strip is normally attached to the patient's permanent record (included in hardcopy format in the patient's folder). While this method is indeed cost effective and simple, it is transportable only in hardcopy format from the primary care physician to any referred physician or other health care provider. For instance, if a patient is referred to a specialist who will require a copy of the ECG, the hardcopy will either need to be sent beforehand or the patient will need to carry a copy of the hardcopy record with him or her to the referred physician's location. Alternately, the primary care physician can send an electronic facsimile of the ECG record to the recipient physician (or hospital, or surgical center, etc.). This obviates the need to carry hardcopy. However, the copy is still retrieved on the receiving end in hardcopy format only.

While analyzing an ECG waveform is a relatively simple task, it is often worthwhile to perform analysis on the waveform or to store the waveform in an electronic repository for remote viewing, later viewing, or off-line and remote on-line analysis. Hardcopy ECG records cannot be analyzed automatically, nor can they be transformed easily into other electronically readable formats other than simple images files, such as bit maps or in JPEG (Joint Photographic Experts Group) format. These electronic formats, while easily transferable cannot be analyzed using on-line mathematical methods, in real time from a remote location.

Accordingly, a system is needed that is capable of producing Web-based rendering of ASCII (American Standard Code for Information Interchange) formatted ECG data, and then transforming and analyzing ECG paper strips automatically via electronic means, which is developed using conventional development programming languages, such as standard C++ and Visual Basic, so that it can be easily integrated into existing software systems. Research into prior or related art reveals that some existing functionality in the area of image scanning and plotting is available on the open market. Specifically, existing art relating to the following functionality is available. For example, relative to transforming hardcopy graphs into electronic (or ASCII) data, Un-Scan-It by Silk Scientific Software (www.SilkScientific.com) is a representative product that enables reading hardcopy (x, y) graphs from scanners and extracting the component coordinates of the plot curve. Silk Scientific advertises on their Web page that allows a user to automatically convert hard copy graphs to (x,y) ASCII data at Full Scanner Resolution. UN-SCAN-IT works with any full page scanner, hand scanner, or other image input device to digitize strip charts, instrumental output, old graphs, published graphs, etc. In addition to the many digitizing features, UN-SCAN-IT also integrates peak areas, smooths data, takes derivatives, re-scales graphs, and exports (x,y) ASCII data for use in other software programs. Another example is an existing modification to a method described by Marv Luse in Bitmapped Graphics Programming in C++ relative to reading bitmap images) extracts the ASCII (x,y) coordinates of a bitmap image. The method for opening the image file was adapted from an existing piece of software by Luse in order to accomplish this latter function. A method also exists for reading bitmap images using Java code for the purpose of altering the images and is described by Joseph L. Webber in *Special Edition Using Java 2 Platform* Copyright 1999 by QUE. However, these systems of the prior art have several significant disadvantages. A system is needed that is portable, and integrates directly with standard word processing tools (such as Microsoft Excel and Word); and that performs processing on a server platform and delivers the finished plot to a client, in accord with the details specified in the claims.

The ability to display plots of ASCII (x, y) data on client platforms using client-side interpreted code, such as JavaScript or VB Script, is described by Ronald H. Nicholson in a JavaScript Plotter published in 1996. The functions developed by Nicholson may be used to create a server-side version of the plot specifically designed to read ASCII data (as opposed to operating on hard-coded functions, as is described in Nicholson's code) and to plot the coordinates of an ECG trace within a Web browser window. For reference purposes, this method will be termed the Server-Side Plotting Utility, or SSPU. An additional utility may also be developed that transmits ASCII coordinate data to a client, where a Java applet then reads the data and plots them within the Web browser window. For reference purposes, this method will be termed the applet Plotting Utility, or APU.

The needed advantages described above can then be accomplished in two ways: raw ASCII (x, y) data can be written to an array on the Server and are transformed into a plot within the client's HTML (Hyper Text Markup Language) page, such as by using an SSPU; or, raw ASCII (x, y) data can be written directly to the client where they are interpreted by a client-side function that performs the process of plotting, such as by using an APU

SUMMARY OF THE INVENTION

The present invention is directed to a system for converting a graphical trace of acquired patient data into digital data suitable for digital signal processing, which includes the steps of receiving data representative of an image including the graphical trace of acquired patient data; analyzing the received data to identify individual pixels comprising the graphical trace in the image representative data; generating a plurality of pixel representative data elements in a desired data format identifying the relative location of the individual pixels in relation to a reference point; generating the desired data format by identifying the relative location of the individual pixels and identifying at least one of, (a) color of said individual pixels and (b) luminance amplitude of said individual pixels; and storing the generated pixel representative data elements in a file. In addition, the received data may be formatted into a format compatible with a procedure located at a remote destination, wherein the procedure is for processing the data representative of the graphical trace to provide processed data suitable for use in presenting the graphical trace in a displayed image; and communicating the formatted data to the remote destination in response to a user command; and generating the displayed image at the remote destination using the formatted data.

BRIEF DESCRIPTION OF THE DRAWINGS

FIG. 19 is a computer screen shot of an Excel spreadsheet window with non-ECG-specific data entered and cell region highlighted used in the present invention.

DETAILED DESCRIPTION OF THE PREFERRED EMBODIMENT

The present invention will be understood more fully from the detailed description given below and from the accompanying drawings of preferred embodiments of the invention; which, however, should not be taken to limit the invention to a specific embodiment but are for explanation and understanding only.

The present invention is directed to an integrated software system for translating hardcopy clinical patient signals, such as ECG or EEG paper image renderings, into ASCII data for the purpose of enabling signal processing analysis using standard PC-based tools. The invention translates the hardcopy ECG or EEG imagery into softcopy by which the softcopy image can be analyzed using signal and data processing functions. The image can be stored and then be displayed using Web-based server processing methods.

The preferred embodiment of the invention described below involves the processing of a hardcopy ECG image through display of that image via its raw ASCII coordinates in a Web browser using an Active Server Page (ASP) application. The embodiment describes two distinct methods for delivering the ASCII coordinates in the form of plots to the client. The first of these is the SSPU and the second is the APU. These ASP methods may be generalized to support a more general product. The embodiment was developed in C++, Java, and Visual Basic using MS Visual Studio and JDK1.3.1. This allows the system of the present invention to be easily integrated as part of other applications. However, one of ordinary skill in the art will appreciate that this embodiment is for purposes of illustration only.

FIGS. 1–12 illustrate the ability of the SSPU and APU components of the invention to read, process, and display ECG image information to a client screen. FIGS. 13–18 illustrate the capability of the ReadBMP component of the invention to read, extract specific pixel color values from, and to create new bit map files. FIGS. 19–26 illustrate the capability of the APU component of the invention to read ASCII data and create simple plots together with an automatic curve fitting function included in the utility.

Figure 1:
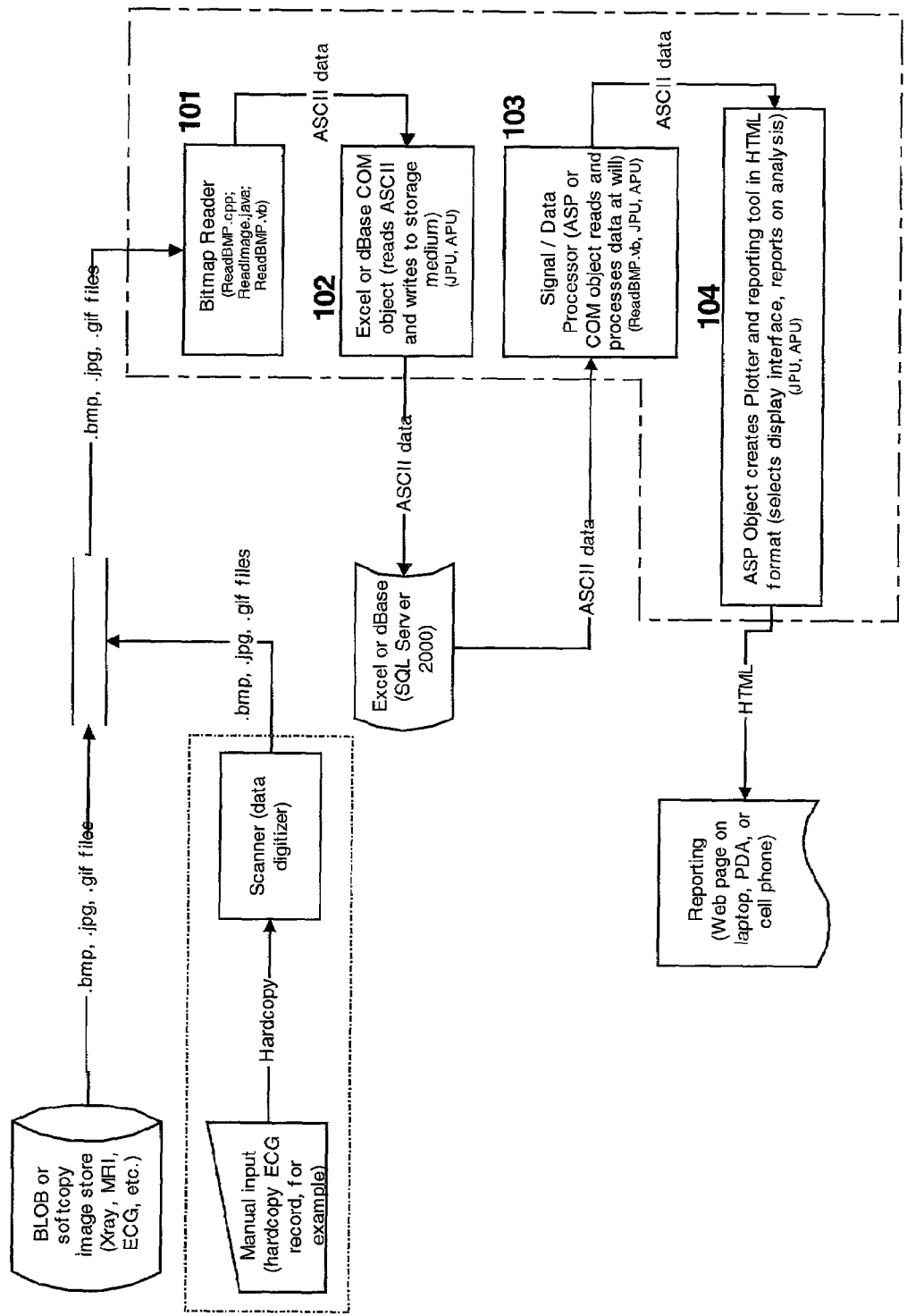
FIG. 1 is a flow chart of the operation of the preferred embodiment of the present invention.

Processing the data from this point will proceed in accord with the data flow diagram provided in FIG. 1. As shown in FIG. 1, the manual input of the ECG (in hardcopy format) to a scanning device (such as a facsimile machine) is shown in the rectangular outline 101 in FIG. 1. The product of the facsimile scan is a bitmap file (.bmp), although other acceptable formats could include .gif or .jpg (.jpeg). The creation of such a file is well known in the art and will not be elaborated upon further here. Once the bitmap file is created, it is retrieved by a BitmapReader program of the present invention, embodied in Image Reader 101. The purpose of BitmapReader is to open the raw binary .bmp file and to determine the location of all pixel values. The BitMap Reader is defined in the current embodiment in the form of two separate utilities: one Java utility entitled ReadImage.class and one Visual Basic utility entitle ReadBMP.vb. The bitmap is retrieved and translated into ASCII, preferably having the following format: $(x, y, color)_i$, where (x) represents the x-coordinate position of the i-th pixel; (y) represents the y-coordinate position of the i-th pixel, and color represents the RGB color of the i-th pixel. Normally in bitmap files and other graphic file formats, the coordinates of the $1^{st}$ pixel correspond to the position (x=0, y=0), or (0,0). This represents the position in the top left-hand most corner of a .bmp file. The coordinates of the last pixel correspond to the position $(x=x_{max}, y=y_{max})$, or $(x_{max}, y_{max})$. This represents the position in the bottom right-hand most corner of a .bmp file.

Figure 2:
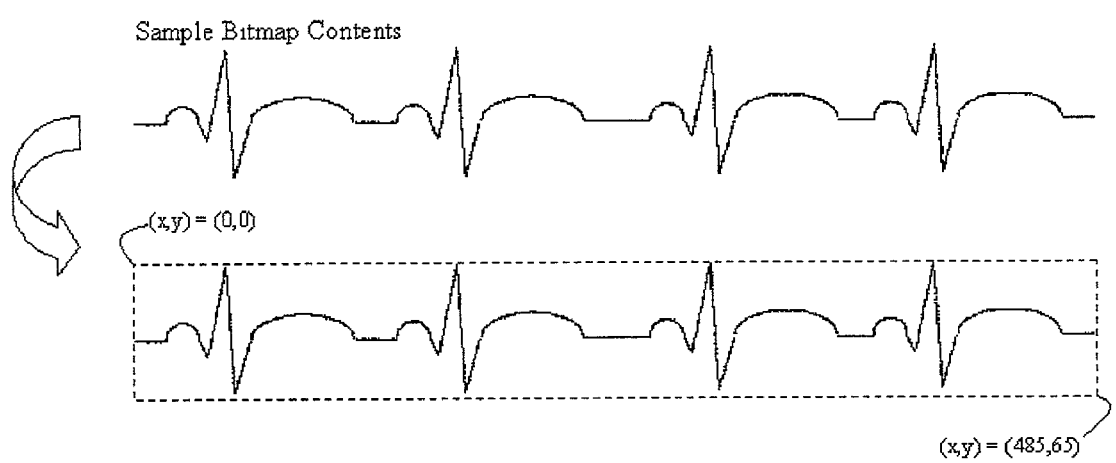
FIG. 2 is a computer screen shot of a sample ECG bitmap image displayed remotely on a client computer.

To illustrate the process to this point, consider the sample bitmap file, shown in FIG. 2. The sample waveform of FIG. 2 is rendered in the form of a .bmp file, created by scanning the original paper image. The image reader of the present invention may be implemented in a number of ways, such as by reading the pixels from a bitmap file in a conventional manner. The process for setting up a structure for reading the header information is not included as it is available in several sources, such as Marv Luse, *Bitmapped Graphics Programming In C++*, Addison-Wesley 1993 and James D. Murray and William van Ryper, *Encyclopedia of Graphics File Formats*, 2nd Edition; O'Reilly & Associates, Inc. 1996. The code segments presented employ the method of the first reference to read in an arbitrary bitmap. The code shows explicitly how the ASCII components (x,y, color) are identified.

Alternatively, a Java applet utility program code segment may render individual pixels from an image file (such as a .jpg file). This computer program may be based on an applet described in Joseph L. Webber, Special Edition Using Java 2 Platform; Copyright 1999 by QUE. However, the extraction of the pixel values and the method for writing to an output file would be modified in accordance with aspects of the present invention.

Figure 3:
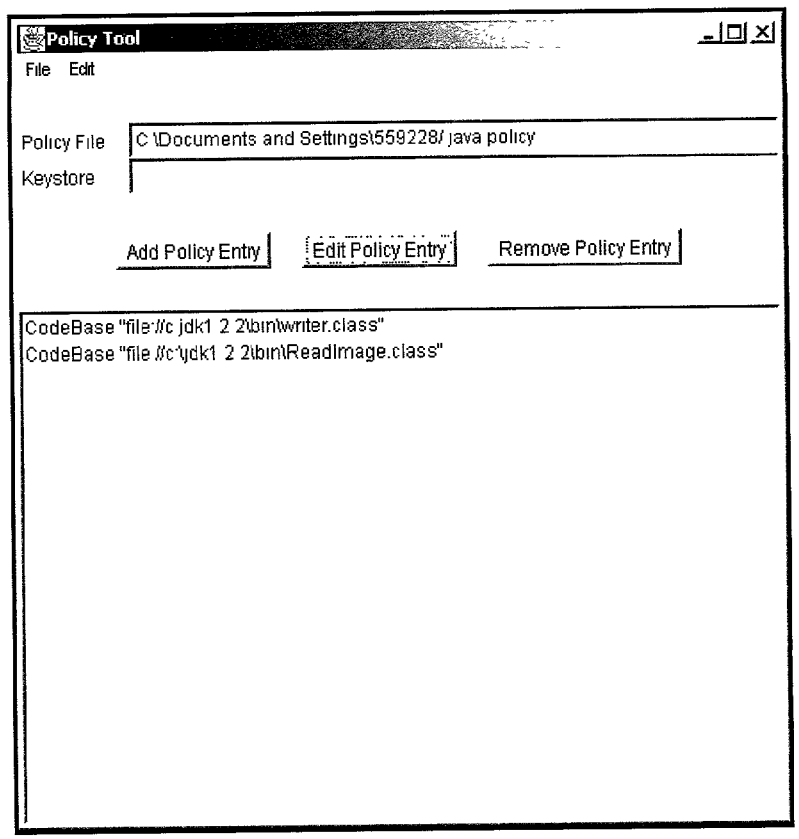
FIG. 3 is a computer screen shot of a sample security policy file contents to enable an applet to write to a file.
Figure 4:
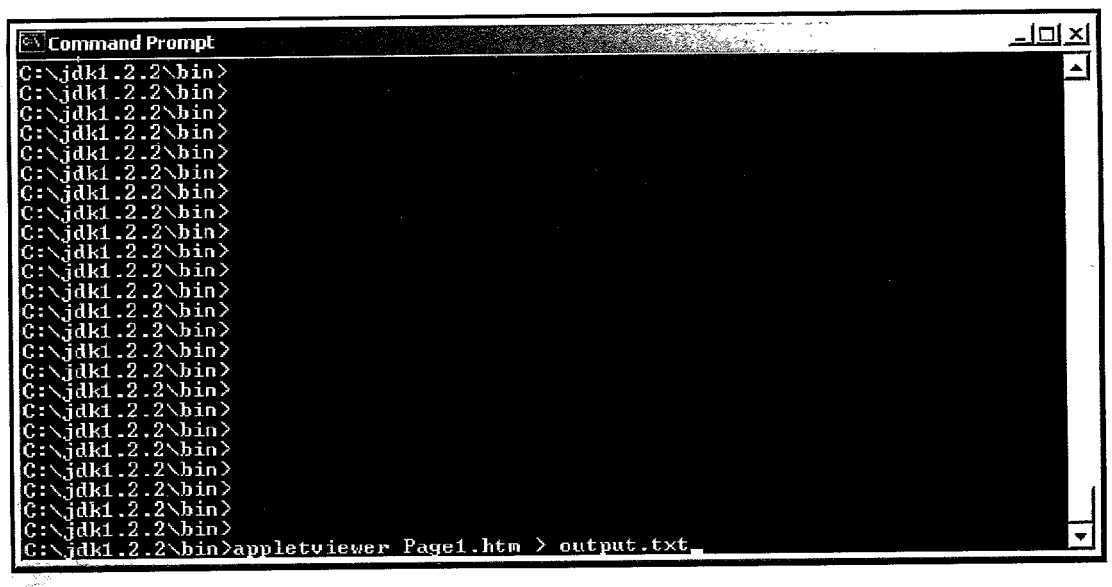
FIG. 4 is a computer screen shot of an appletviewer execution of the ReadImage applet of the present invention.

In order for the applet of Data Object 102 to write to a file, it is necessary to set the policy file on the computer system being used to allow write access. A sample policy file associated with this applet is illustrated in FIG. 3. FIG. 3 is a computer screen shot of a sample security policy file contents to enable an applet to write to a file. This file is used by an applet to write the (x, y) coordinates of the bitmap image to an ASCII text file, which is then read by a post-processing tool and stored in MS (Microsoft) Excel. Note that the ASP (Active Server Page) version of this image reader does not require a security policy file as the ASP version executes on a server. An applet version of this method was illustrated here to demonstrate the capability of reading the ASCII (x, y) data points from a bitmap image. And, FIG. 4 illustrates a sample command window showing execution of the applet via the JDK appletviewer command tool and the writing of the applet to an output file named output.txt.

Figure 5:
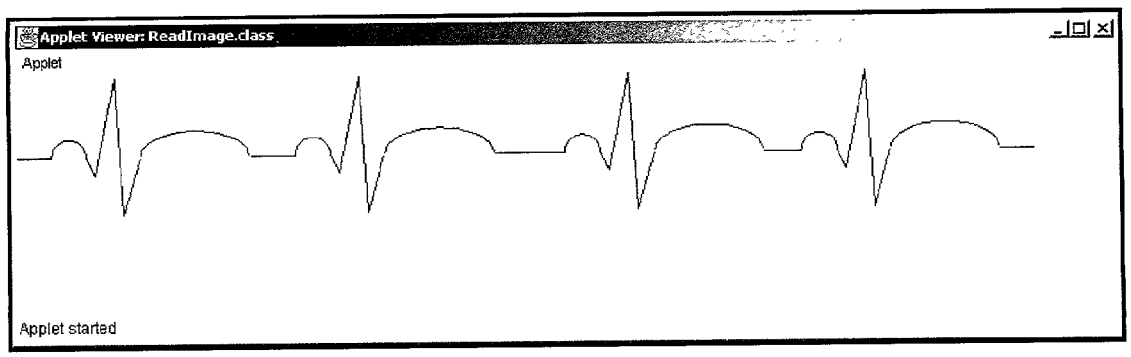
FIG. 5 is a computer screen shot of an appletviewer rendering of ReadImage inside of an HTML file of the present invention.

Upon execution of the applet utility, the appletviewer renders, or echoes, the original image applet) as specified in the applet. This image rendering is not required, but merely serves to verify that data were correctly read by the applet. This is illustrated in FIG. 5.

Figure 6:
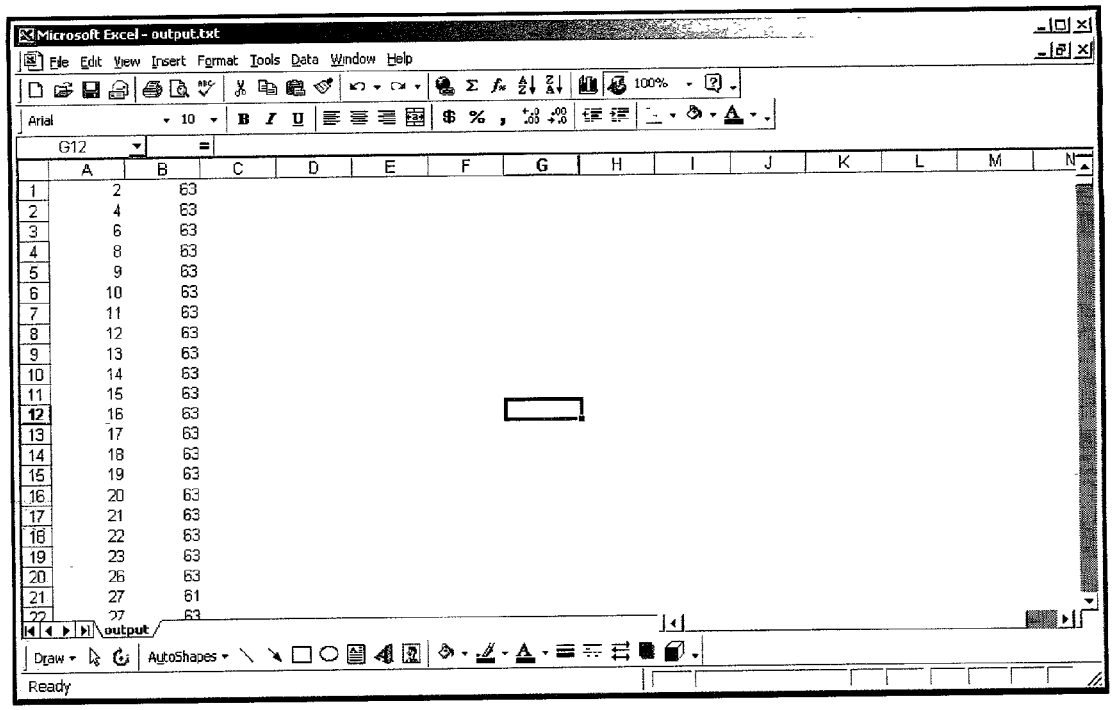
FIG. 6 is a computer screen shot of data from a file containing an image rendering of an ECG written to text and imported into MS Excel in the present invention.

The ASCII text data now exist in a file (output.txt). The contents of this file can be written by Data Object 102 using either of the methods defined above (that is, in C++ or Java), or any other method. Once available in text form, the data can be imported directly into either a database or a spreadsheet. An example of these data as they exist in an Excel spreadsheet is as shown in FIG. 6. These data were generated using a java applet.

Figure 7:
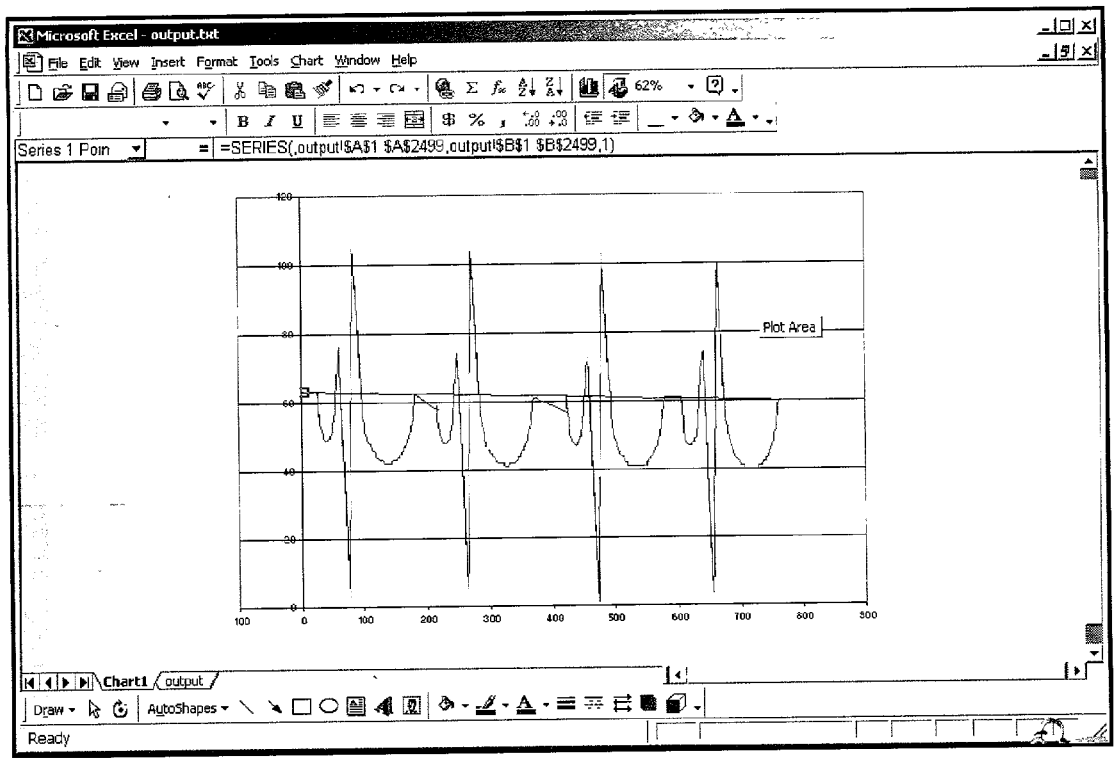
FIG. 7 is a computer screen shot of a plot of pixel values in the present invention drawn using the raw data captured by the readBMP utility within MS Excel.

To illustrate the content of the data, a simple plot was generated by Signal Processor 103 and Imaging Object 104 using the pixel values to illustrate that indeed the data are representative of the original ECG image. This is shown in FIG. 7. FIG. 7 is a computer screen shot of a plot of pixel values in the present invention drawn using the raw data captured by a utility within MS Excel. These are the same data points as shown in FIG. 6. Upon reading the data, y-component elements are reversed (because the (0,0) element represents the top-left-hand of the screen in the image file, and the maximum extent of the image file, defined by the point (xMax, yMax) is the bottom right-hand corner) so the image appears flipped vertically. This is rectified by the ASP post processor.

Sample pixel values are plotted to illustrate reconstruction of ECG waveform. Importing the data directly into an Excel spreadsheet can be accomplished with the aid of any program that can establish a connection via a COM interface to Excel, or can be accomplished in ASP using an ADO interface. An MS Visual C++ program is one example of how to accomplish this goal. The result of running this program is an Excel spreadsheet file, which contains two columns of data: the x and y pixel coordinates of the ECG.

Figure 8:
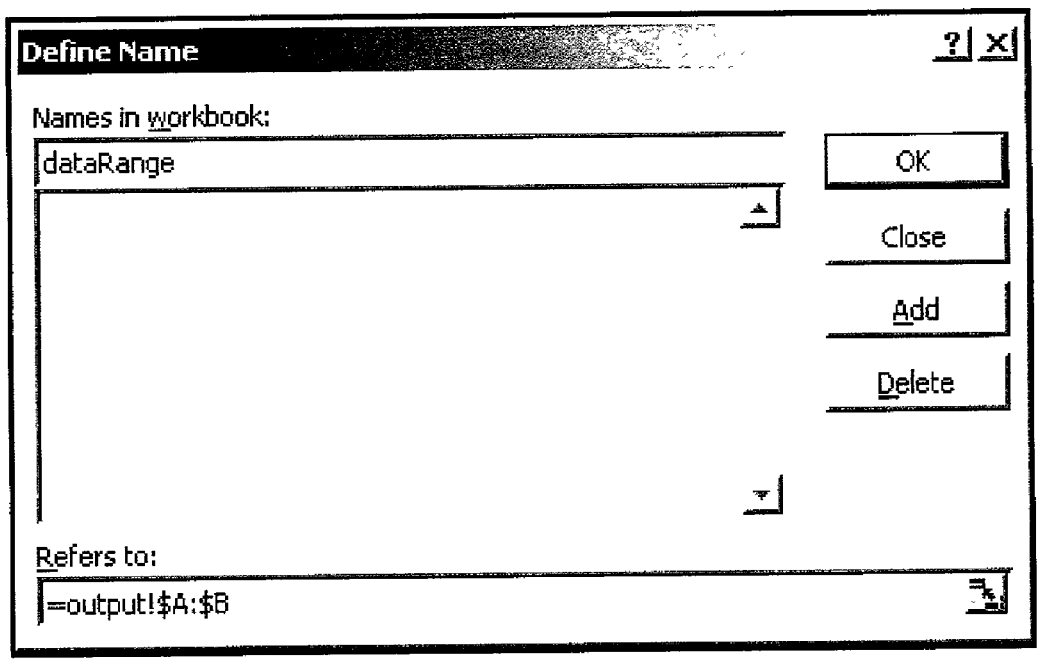
FIG. 8 is a computer screen shot of setting the data range and defining a name in preparation for reading in the data to be processed by the present invention.

In Excel, a named range must be defined so that an ASP can read the data via an ODBC driver. An example of the named range of the data is shown in FIG. 8, and corresponds to columns A and B within the Excel spreadsheet (that is, the 'X' and 'Y' pixel ranges). FIG. 8 is a computer screen shot of setting the data range and defining a name in preparation for reading in the data to be processed by the present invention. This defined named range enables an Active Server Page (ASP) to read directly from the MS Excel file using the handle provided by the named range specified in the figure. The named range is employed by the Open Database Connectivity (ODBC) manager to link the contents of the MS Excel file to the ADO (ActiveX Data Objects) used within the ASP so that the contents of the MS Excel file can be read automatically. The output in this embodiment must have the column labels inserted, which may be included in the MS Visual C++ program output for titles, as shown in previously mentioned program code.

Figure 9:
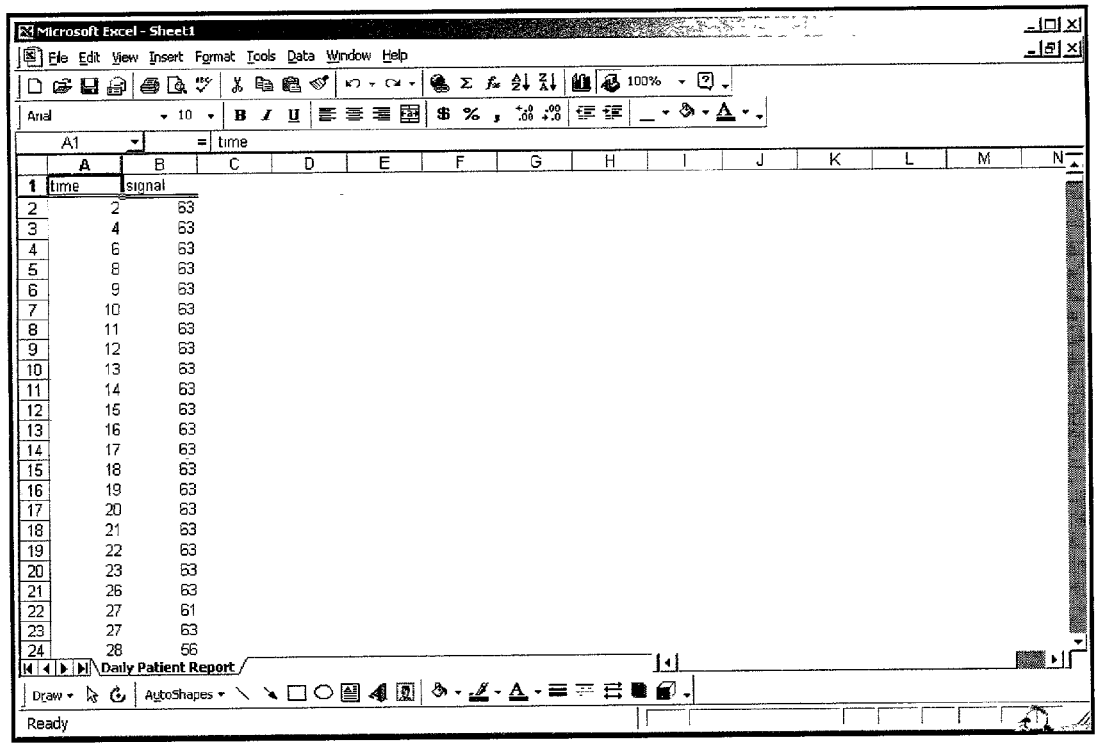
FIG. 9 is a computer screen shot of an updated MS Excel spreadsheet illustrating required column names in the present invention.

This is shown visually in FIG. 9. It is now possible to process the raw data using a server-side script of Signal Processor 103 and Imaging Object 104, such as an Active Server Page (ASP). FIG. 9 is a computer screen shot of an updated MS Excel spreadsheet illustrating required column names in the present invention. When reading MS Excel data using an ADO within an ASP, the first row of data within the Excel spreadsheet is automatically interpreted as the labels of the associated spreadsheet columns.

The ASP program retrieves the spreadsheet data and displays using the intrinsic Excel mathematical and statistical functions to process the data and then to write the processed result to the Web browser. In this way, processed results may be disseminated to a desktop or laptop computer, Cell Phone, or PDA in formats consistent with these devices.

The ASP program produces tabular values of the pixel coordinates associated with the bitmap. However, more interesting is the display of FIG. 10, that may be produced by the ASP program. This program combines the ODBC reader of the previous example with a VBScript plotter. The methods make_1d_array, make_2d_array, and plot_2d disclosed in Ronald H. Nicholson, Javascript Function Plotter, published in 1996, and may be modified and used to achieve the present invention. This utility is preferably embodied in the SSPU.

Figure 10:
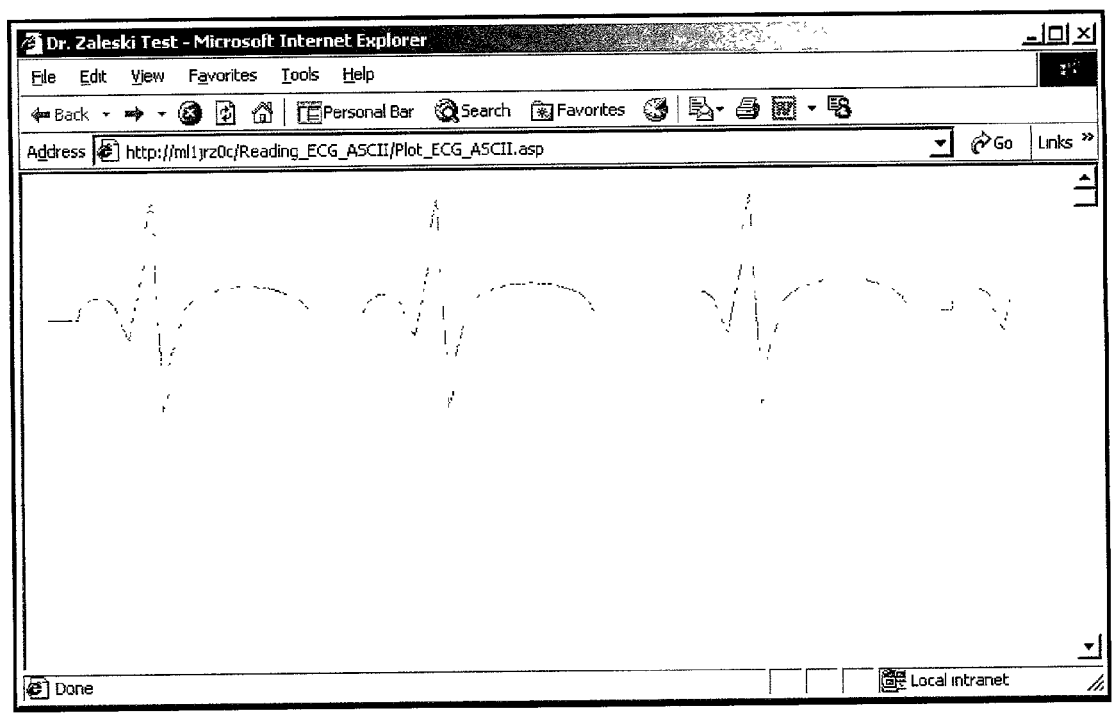
FIG. 10 is a computer screen shot of a Web browser plot of a subset of data from the original bitmap file in the present invention using the SSPU.
Figure 11:
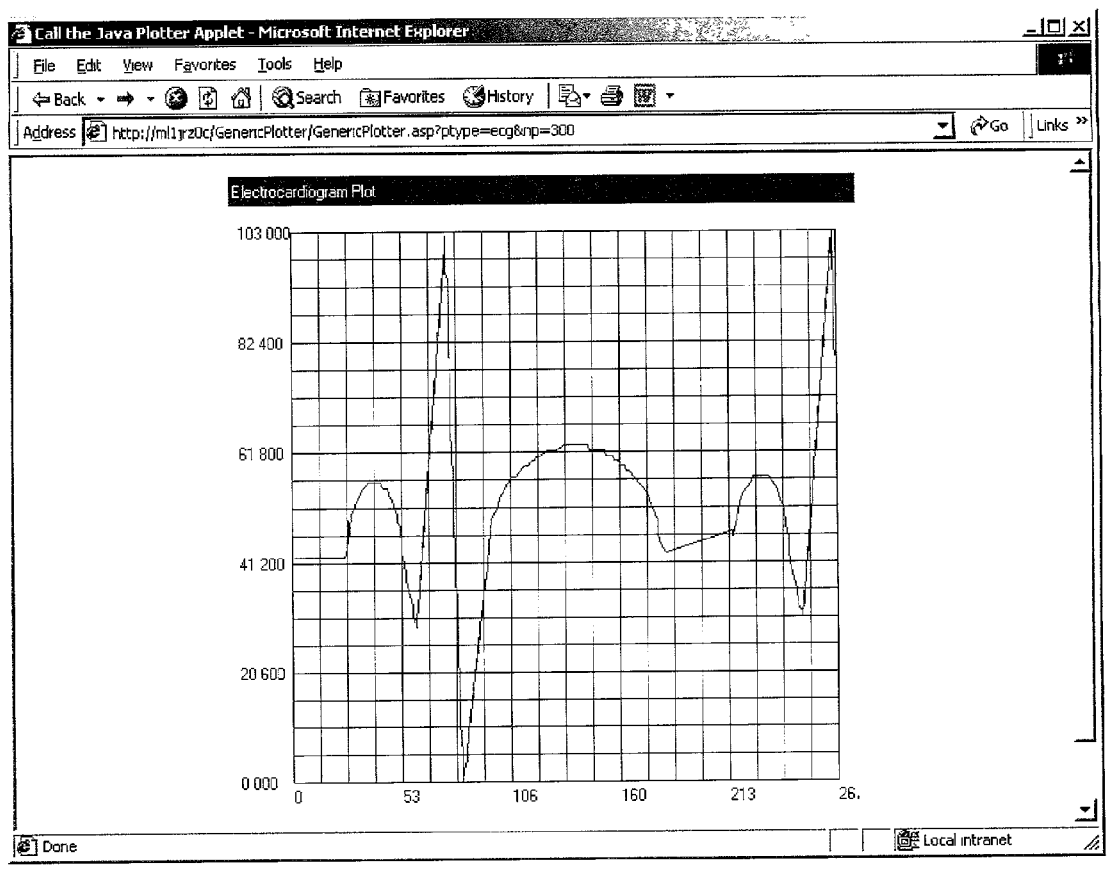
FIG. 11 is a computer screen shot of a Web Browser plot of a subset of data from the original bit map file in the present invention using the APU.
Figure 12:
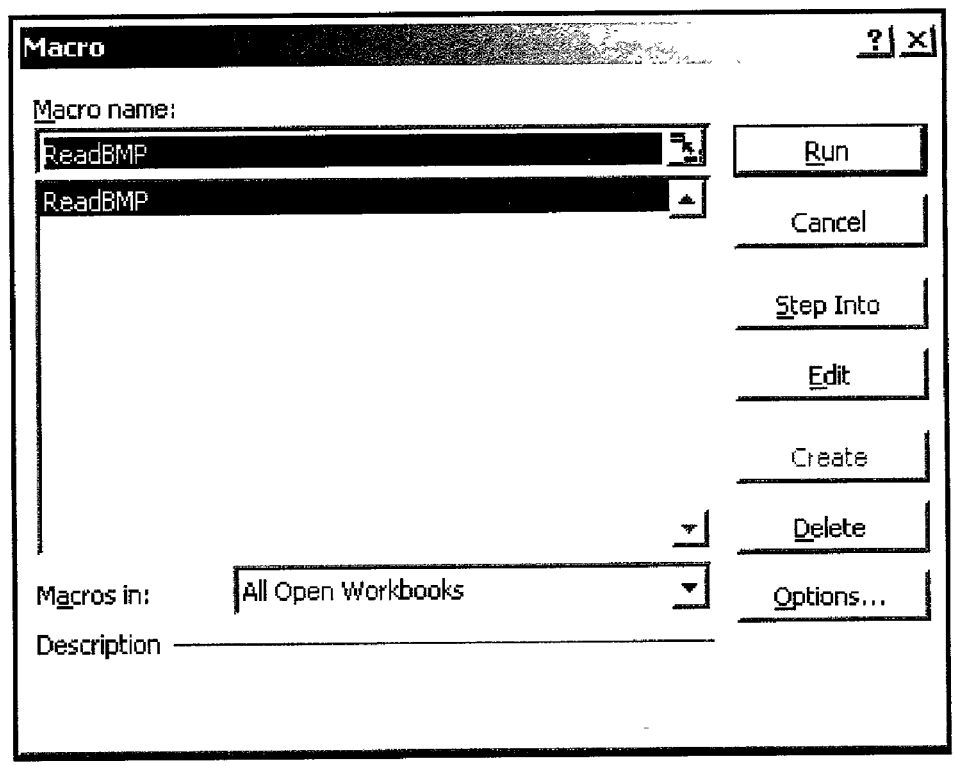
FIG. 12 is a computer screen shot of creating a new macro in the present invention that extracts the ASCII (x, y) data from the bitmap or JPEG file.

It is important to note that this use of ASP code is for purposes of illustration only. For example, the code described above contains hard values for specific image sizes. However, to make this code more portable and general, it must be able to accept an arbitrary size image. This code is tailored to support only the specific size image for the worked example. The implication is that the code can only (presently) support an 800×800 pixel image, but the present invention is not limited thereto. Naturally, the code itself must be made more flexible to be able to support any ECG trace of any size and to display the data desired by a user. The purpose in showing FIG. 10 is to illustrate that, via a Web interface, the user has access both to the raw data points and to the image itself.

In the APU, a client-side plotting function preferably reads the ASCII data values transmitted to it by a server-side application (ASP). The client utility produces the plot shown in FIG. 11.

In a further embodiment of the present invention, 24-bit color image files can be read for purposes of analysis, and generated from data and analyzed results. This aspect of the present invention may be accomplished, for example, as a macro built within an Excel spreadsheet, but those of ordinary skill in the art will appreciate that the present invention is not limited thereto.

To carry out this aspect of the invention using the aforementioned macro, the user needs to launch Excel, although the reason for this is that the utility, ReadBMP.vb, integrates its processing of the output data with Excel spreadsheet utilities. In other embodiments, this utility need not be integrated within Excel in order to function in its basic role of reading the ASCII pixel values.

The process of creating this utility is summarized here to clarify the process of its creation. Once Excel is launched, the user would select Tools from the file menu and select Tools→Macro→Macros. The user will be presented with a window, as in FIG. 12, in which he/she may type the name of the macro. The macro illustrated herein has been designated as ReadBMP.

The visual basic macro itself opens a 24-bit color bitmap using the "Open For Binary Access Read" statement, as follows: "Sub ReadBMP( ) [Intermediate code removed] Open [filename] For Binary Access Read As #1". Here, [filename] corresponds to the fully qualified path and name of the bitmap file. If this value is hard-coded, then the user will have to save the program and make changes every time a new file is to be read. Therefore, in the embodiment of the present invention, the user may enter this information in a worksheet—called Input_Sheet—that is read by the macro. The file name is then read from the input worksheet dynamically. In this way, the user can enter any file name desired without altering the macro itself. This input file worksheet is shown in FIG. 13.

Figure 13:
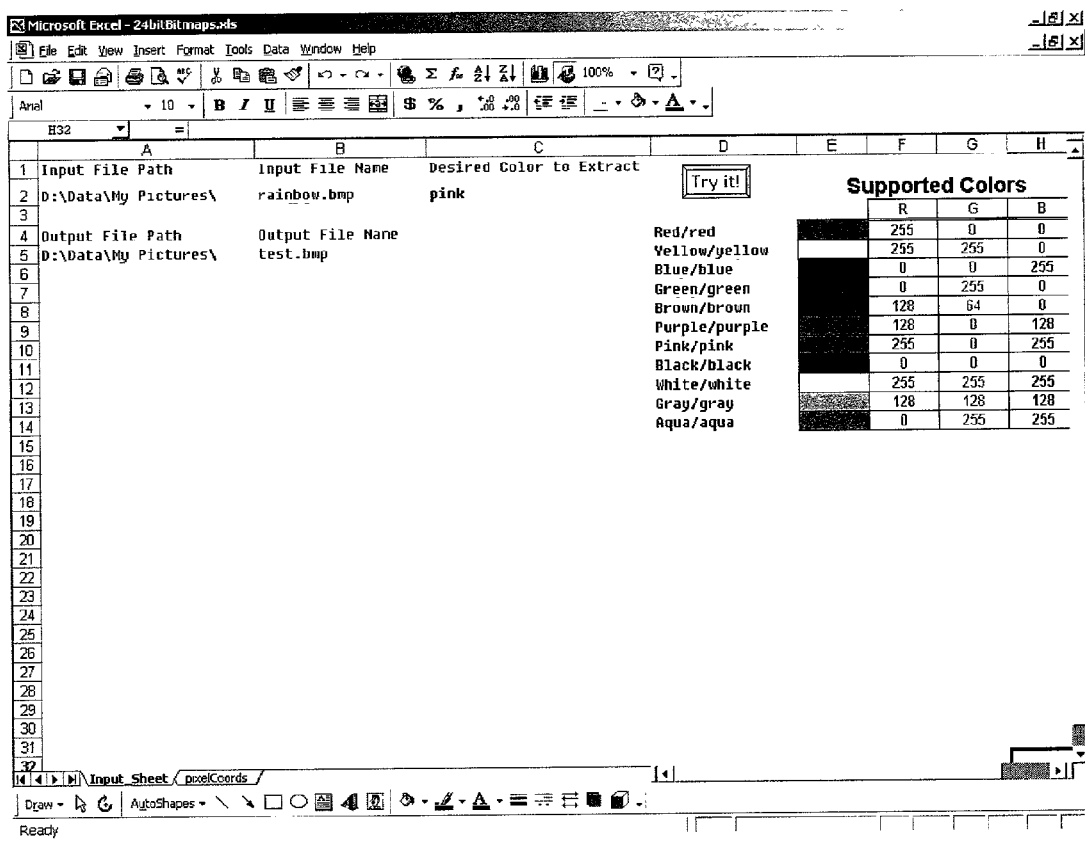
FIG. 13 is a computer screen shot of an "Input_Sheet" data input window used in the present invention by the ReadBMP utility to extract the pixel data from the bit map file.

As shown in FIG. 13, the File Path and File Name cells identify the location and name of a particular bitmap file. In this case, the file path is "D:\Data\My Pictures\" and the file name is "rainbow.bmp" (this file is used to illustrate the flexibility and capability of the ReadBMP utility to access individual pixels of various colors from the bitmap file). Thus, in the utility itself the generic [filename] may be replaced with specific code that can read these cells from the particular workbook. Here, the String variables ifpath, ifname, and ifiles merely identify the path, file name, and concatenated file path and name, respectively, of the bitmap to be read by the utility. Similarly, the output path (for writing to the binary output file) is defined in a similar manner. In the example shown, all ASCII data are written to a worksheet entitled "pixelCoords". Therefore, all pixel data will be saved to this spreadsheet.

Once the bitmap file is opened for read access, it is necessary to read in the individual elements of data. Because the file is opened for binary access (as is necessary when reading bitmap or other image files), the individual elements of data will be read from the file in the form of bytes. This is accomplished in the example program code by declaring a variable, x, as being of type Byte: Dim x As Byte. The variable, x, may now be used to read in all elements of data from the file. In order to do so, the header information must first be read from the bitmap file. The header provides information regarding the bitmap's height, width, and color scheme (that is, 24-bit, or 8-bits per each color—Red, Green, Blue). This information is used by the macro to determine when, in reading these data, the end of each line of pixels has been reached.

First, the width and height of the bitmap must be determined. Each byte is read from the bitmap file using the Get command. The Get command reads the file unit number (defined as #1), the record number (optional), and the actual data (defined as x). The 19th element read from the bitmap file represents the height of the bitmap. The records read from the bitmap are tracked using two counting variables: amt and recNumber. The variable 'amt' is used to keep track of where in the bitmap the program is, while the variable 'recNumber' is used to write the pixel data to the new bitmap file. The width is read, which is separated from the height by three bytes, and then the depth of the bitmap is read. This defines the depth as being 24 bits: one 8-bit segment for Red, one 8-bit segment for Green, and one 8-bit segment for Blue. Thus, the color of any given pixel value is given by {RGB}, where R varies between [0 . . . 255], G varies between [0 . . . 255] and B varies between [0 . . . 255].

Next, the start of the first pixel within the bitmap is read. And, the entire bitmap is read in this manner at this point. The 'amt' variable is preferably re-initialized to 1 to keep track of how many data elements are being read. It is read byte by byte into the variable x. The row and column location of the pixel is tracked by noting the quantity of pixels read in relation to the height of the bitmap. For every row and column pixel value, there correspond three values: an R-value, a G-value and a B-value (0 . . . 255,0 . . . 255,0 . . . 255). Pixel color selection and identification has been automated by incorporating a code segment that enables the operator to state (using the associated color word value) a desired color to be sought within the bitmap file. This is illustrated in Table 1. The utility maps the word value for color to an associated {RGB} color byte value, and then uses the associated color byte value to seek for the matching byte combinations within the bitmap file.

TABLE 1

Supported Colors

| | R | G | B |
| --- | --- | --- | --- |
| Red/red | 255 | 0 | 0 |
| Yellow/yellow | 255 | 255 | 0 |
| Blue/blue | 0 | 0 | 255 |
| Green/green | 0 | 255 | 0 |
| Brown/brown | 128 | 64 | 0 |
| Purple/purple | 128 | 0 | 128 |
| Pink/pink | 255 | 0 | 255 |
| Black/black | 0 | 0 | 0 |
| White/white | 255 | 255 | 255 |
| Gray/gray | 128 | 128 | 128 |
| Aqua/aqua | 0 | 255 | 255 |

To provide the capability to select more colors than these (and the list is effectively unlimited), then it is necessary to identify the three-color byte values and add the appropriate logic to the Visual Basic Macro. One of ordinary skill in the art will appreciate that this process could also be automated too, for example, by reading in the values from a file or by interfacing the utility directly with a visual color generation utility (such as a color palette) in which the user selects an analog color which is then automatically translated into the associated {RGB} byte values.

If the user wishes to select all red pixel values from a bitmap, then the macro can simply be directed to search for a combination of byte values that equal {255, 0, 0}. A description of the code that accomplishes this follows. The file is read in its entirety. The byte values have been read in triples—that is, for each {row, column} pixel value, there are three bytes: one corresponding to red, green, and blue, respectively. Each time a pixel "triple" is read, it is checked to see what "color" it is by evaluating the three byte values against three known values. These values are selected in the Input_Sheet via a field that enables the user to specify the desired color to extract from the bitmap (refer back to FIG. 13). In FIG. 13, the second element of the third column is a user-specified color value: the user types in the selected color, which must correspond to one of the colors shown in the chart on the right-hand side of this sheet. The variables are preferably assigned inside If . . . then statements.

The process by which a raw binary file is opened was described above. The file path and file name are captured using variables. These variables were initialized in the Input_Sheet as shown in FIG. 13. Writing to the new bitmap file is simple: every time a byte is read from the input file, write it to the output file. However, in the case of the output, the specific record number written to the file must be tracked.

As each byte is read from the input file, the values are held in byte variables and the tracking variable is incremented. These byte values are not yet written to the output file. First it is necessary to determine whether the input combination of byte variables matches with the user-specified color, defined by the known color values. Once a color combination has been found that matches with the desired color, these colors must be written to the output file in the correct order. This is preferably begun by writing the B color as the byte element in the (x-2) position, the G color as the byte element in the (x-1) position, and the R color as the byte element in the x position. Once this is done, the tracking variable may be incremented in preparation for reading and positioning the file pointer to the next location within the output file.

However, if a pixel that matches with the desired color is not found, the output file cannot be left blank in that location; the position of the colored pixel location in relation to all other pixels must be maintained. This has been achieved in the example by writing white pixels to those locations that don't correspond to the desired color (note RGB combination: {255,255,255}).

The pixel data is extracted using a binary read method in which the actual size of the file is determined directly from the file header prior to reading the pixel data. This allows for reading of arbitrarily sized files without having a priori knowledge of the image. The raw binary data are extracted in three 8-bit segments per pixel (corresponding to a 24-bit color bitmap) in which the exact knowledge of each pixel color is known and may be used to discriminate actual signals from background noise. Once extracted, the pixels are compared with a user-specified desired color map, which will selectively extract those pixels corresponding to those desired for extraction by the user. The method will then write out the ASCII pixel coordinates of those extracted values and re-create a new bitmap file (in a format compatible with commercial paint or image manipulation programs) containing only the color and geometric reproduction of the user-specified image.

Figure 17:
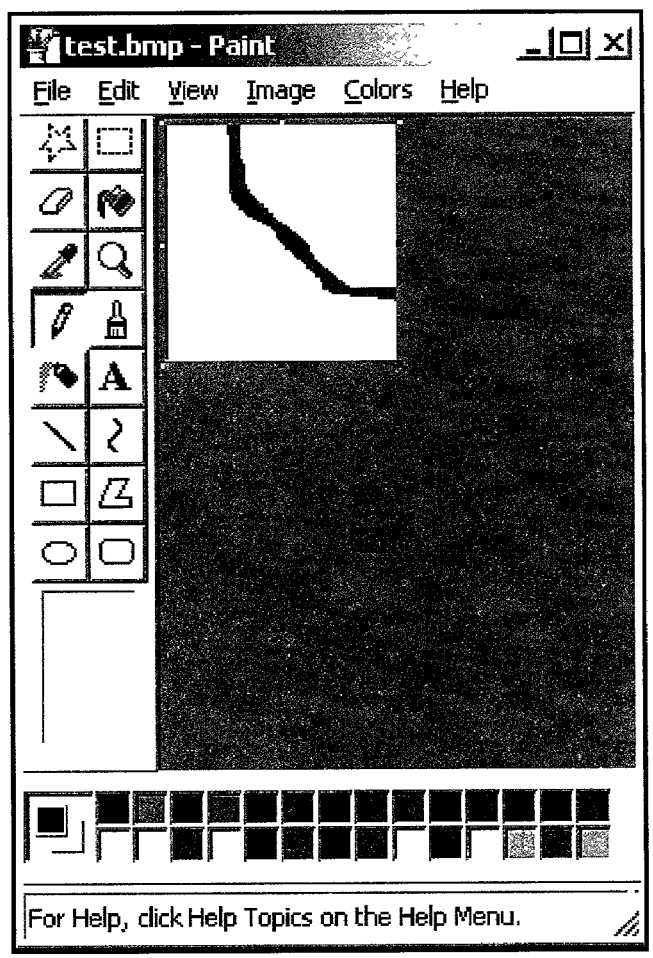
FIG. 17 is a computer screen shot of the content of an image file, called test.bmp in the present invention.
Figure 18A:
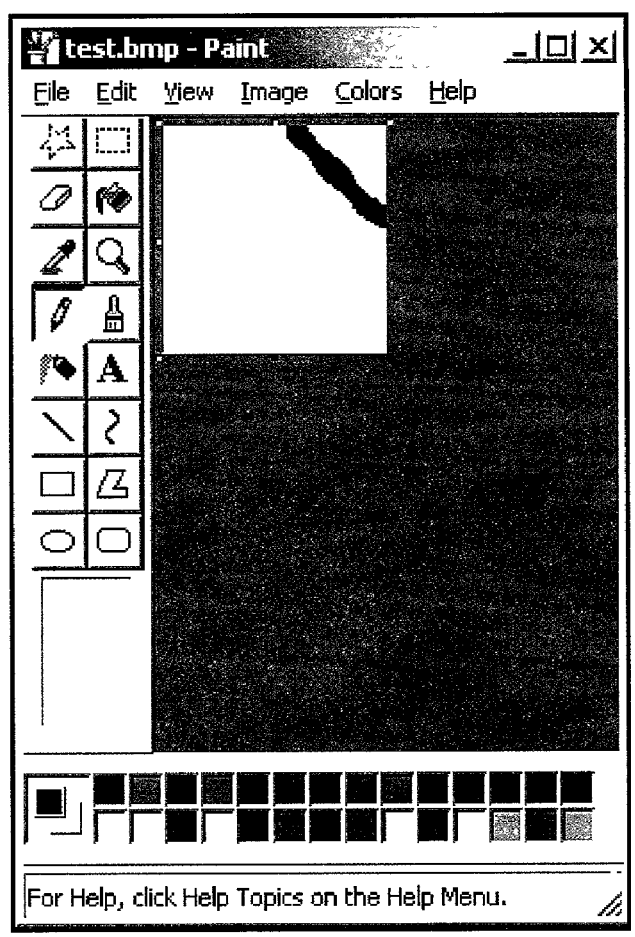
FIGS. 18(a)–(c) are computer screen shots of blue, green, and pink color bitmaps created from rainbow.bmp used in the present invention.
Figure 18B:
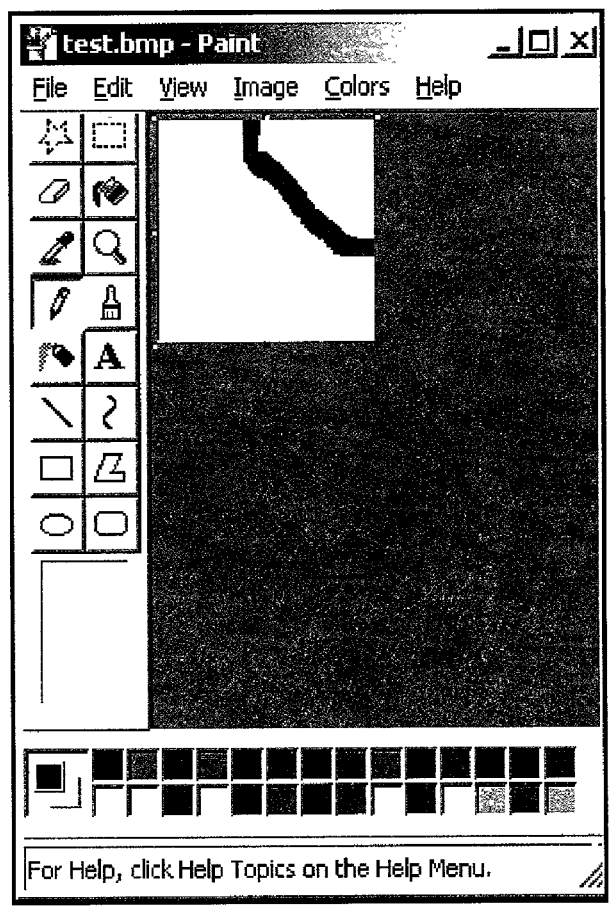
Figure 18C:
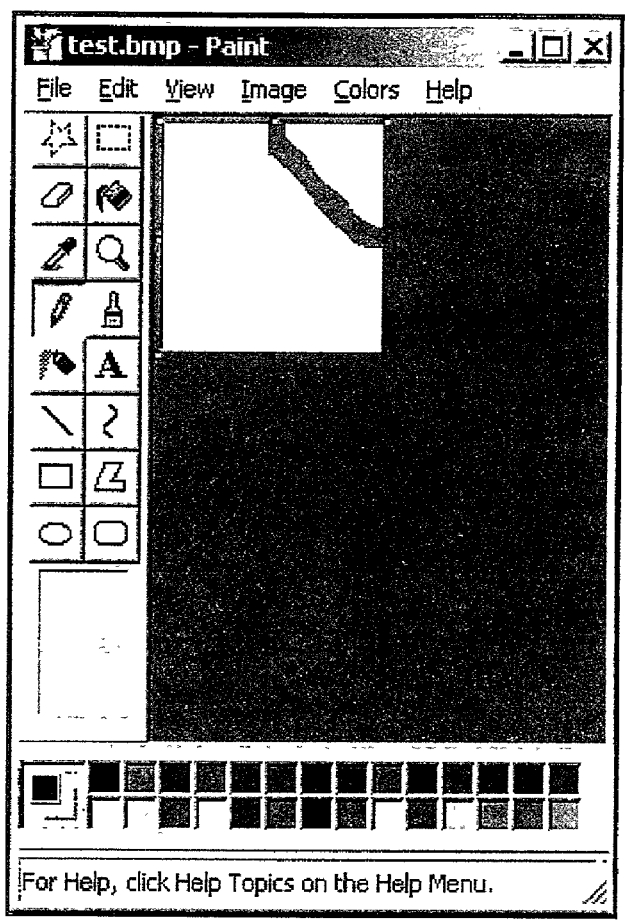

The extracted pixels values represent the two-dimensional (x,y) locations of the user-specified colors extracted from the original bitmap. Given these locations represent the trace of an ECG signal, they may be analyzed to determine frequency (that is, heart rate) electronically from the raw data. Alternatively, individual segments comprising the ECG trace may be studied (such as is necessary when determining ST segment length or for determining whether artifact (noise) exists within an ECG signal). Another advantageous feature of the present invention is the addition of a tracking algorithm to the data extraction method. A tracking algorithm (such as a Kalman or Batch-least-squares filter) allows predicting changes in ECG frequency, ascertaining whether changes in frequency or ECG signal composition are statistically significant (and, thereby, important information for the clinician or care provider), or are normal in comparison with other patients of similar physiological background (body surface area, age, gender, clinical presentation).Capturing the pixel data in this way also facilitates compression of the key signal components for archiving and retrieval of the signal data. For example, by storing only the actual pixel (x,y) coordinate values associated with the signal itself (ignoring unused white space surrounding the signal) reduces the amount of storage required for the actual signal. Furthermore, recreation of the original signal value is accomplished easily since the (x,y) component positions of the signal are stored, and the only remaining task in recreating the actual signal is the placement of filler white space around the signal (as is illustrated in the example of FIGS. 17 & 18(a–c)).

Figure 14:
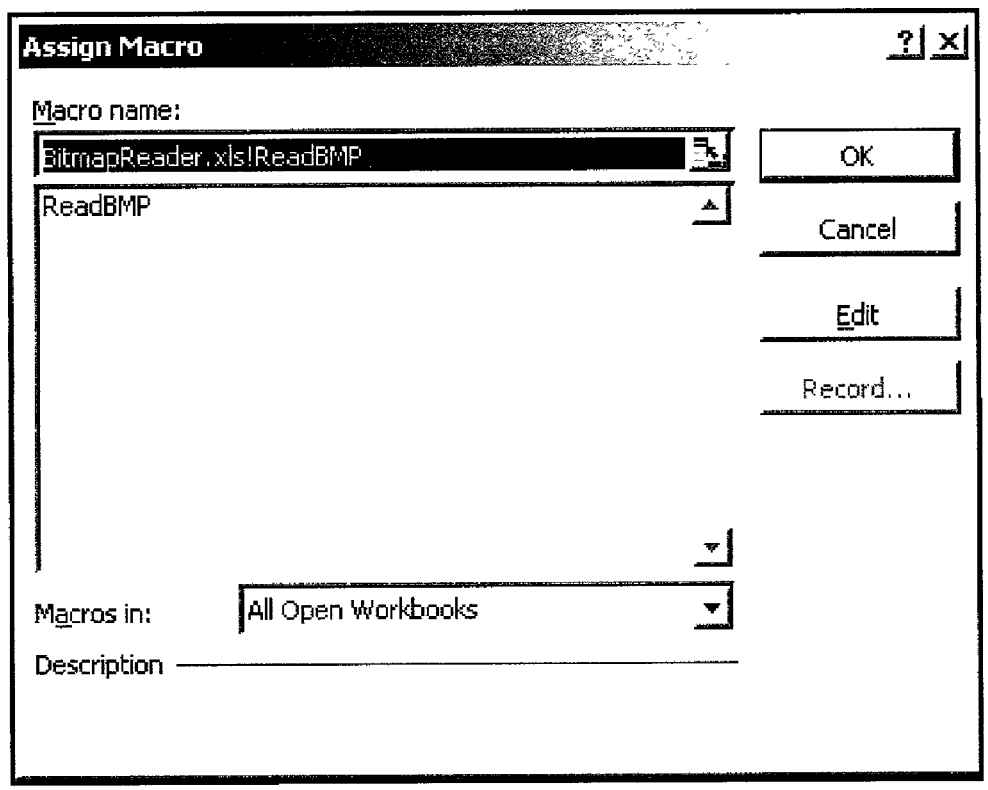
FIG. 14 is a computer screen shot of a macro assignment window used in the present invention.

To enable rapid execution, an AutoShape figure created on the sheet using the Drawing Tool is assigned to the macro ReadBMP. This enables the user to run the utility conveniently from the input sheet. The assignment of the macro to the shape is accomplished simply by right-clicking on the object and then selecting "Assign Macro" from the menu list. A menu window appears, as shown in FIG. 14, and the user then selects the macro and clicks "OK".

In operation, the first thing a user does is to identify the location of a bitmap. This location is entered into the "File Path" cell on the Input_Sheet. The user then enters the name of the bitmap in the "File Name" cell. The user then types in the desired color pixels to extract from the bitmap. Once accomplished, the user simply clicks on the macro button. Depending on the size of the bitmap, the actual extraction process takes anywhere from a few seconds to a few minutes (this performance is also machine processor and memory dependent). Once complete (the cursor will change back from an hour glass to its normal appearance), the user may click on the output sheet. As stated earlier, all output in this example is directed to worksheet sheet 5, although this is clearly not required.

Figure 15:
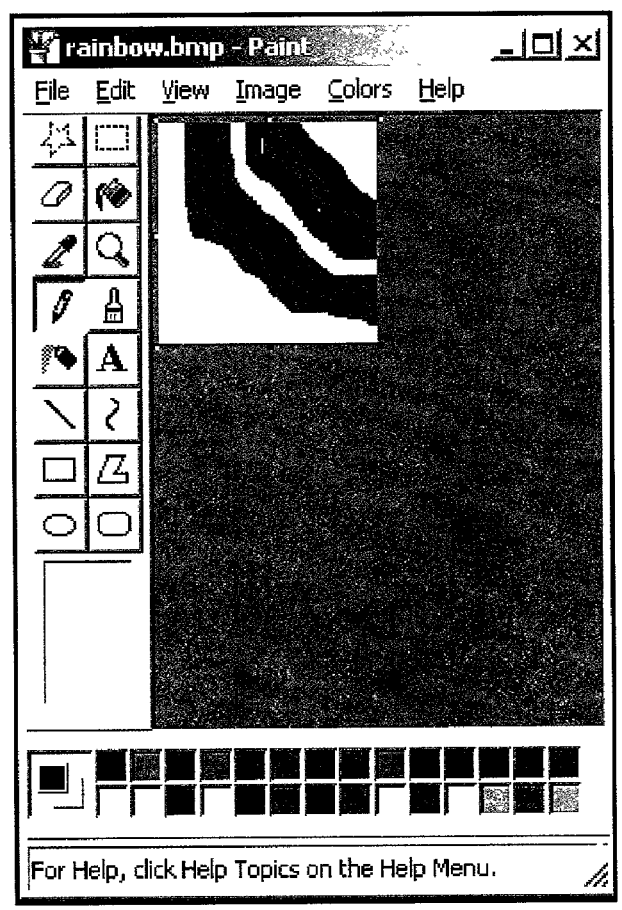
FIG. 15 is a computer screen shot of a bitmap, rainbow.bmp, used in the present invention to illustrate the ability of the ReadBMP utility to extract specific color schemes from the original image.
Figure 16:
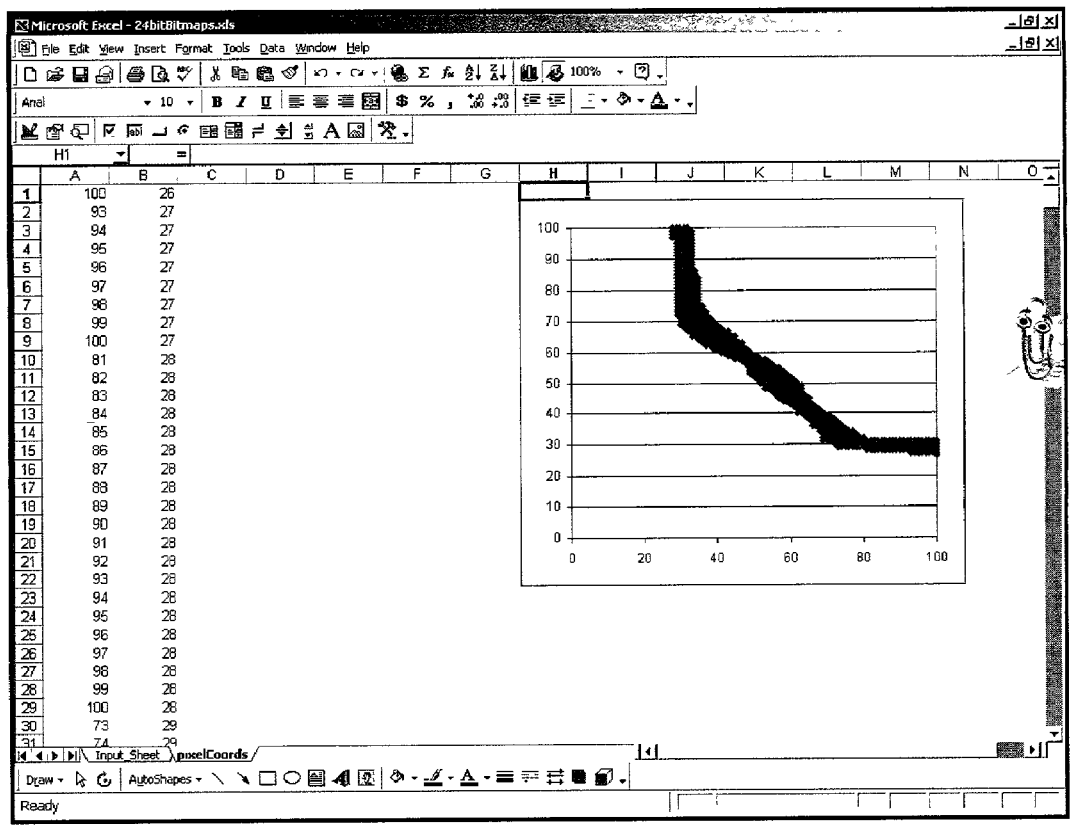
FIG. 16 is a computer screen shot of a processed output from the bitmap file of FIG. 15.

The rainbow.bmp file shown in FIG. 15 was created using MS Paint. The input screen for this example was actually shown in FIG. 13. The color "red" is selected. The corresponding output is shown in FIG. 16. FIG. 16 is a computer screen shot of a processed output from the bitmap file of FIG. 16., illustrating the extraction of a single color from the bitmap file described by FIG. 15 used in the present invention The pixel coordinates associated with the color RED are shown in column format to the left of the plot of those coordinates, provided as a visual aid to verify the correct coordinates have indeed been extracted. Columns A and B in FIG. 16 are the row and column pixel locations for all red pixel elements. Columns A and B have optionally been plotted using the chart tool (selecting XY (scatter)). The plot of these data is shown on the accompanying graph (shown on the right of the worksheet). As can be seen from FIG. 16, the pixel values are a true representation of the bitmap. However, the exact pixel locations are also revealed.

The generated bitmap, test.bmp, is shown in FIG. 17. FIG. 17 illustrates one capability of the ReadBMP utility to re-create a bitmap image of the selected color extracted from the original image. The ReadBMP utility, after querying the user for a particular color choice, provides those coordinates in ASCII format (described in the narrative text of FIG. 16) and then creates a new bit map file using only those coordinates placed at the same location as they appeared in the original bitmap file. This figure is a computer screen shot of the content of this new file, called test.bmp, in the present invention.

The file may also be regenerated with different colors selected. This is shown in FIGS. 18(*a*)–(*c*) with the selection of blue, green, and pink from rainbow.bmp.

The ASCII data may be retrieved from a spreadsheet (or a database) and transmitted remotely to a user, such as by writing the data via an active server page to a client computer in the form of an HTML page. The HTML page would contain a call to a Java applet that then reads the ASCII data and plot the raw data. The applet may also plot overlays of any number of additional (x,y) data sets on the same axes. In the example described below, an application is described in which the applet Plotter Utility (APU) plots the coordinates of a least-squares generated best-fit regression curve on top of raw data supplied by a server side Visual Basic script. This aspect of the present invention obviates the need to perform server-side plotting and passing of either GIF or JPEG images over the Internet. In addition, the active server page determines the best form of the regression curve (linear or quadratic) before writing the data to the client for plotting.

Superior performance may be achieved in terms of transmission of ASCII data (text) over the Internet versus transmitting an image of a plot (created on the server and transmitted to a thin client). Processing takes place on both the server and the client: on the server, data are retrieved from the spreadsheet, are fit to a linear or quadratic equation, and are formatted into an HTML page within applet parameter calls; on the client, data are read and plotted.

Several alternatives for implementing this exist. These include creating a plot using CGI or server-side script and then displaying the image as a GIF or JPG on the client; and hard-coding all data within an applet and plotting entirely using client processing; creating an image using a spreadsheet program and copying the image to a file and then displaying the plot image via an active server page or an HTML page on a client (requires off-line processing to prepare image for display either via active server page or HTML page). Of course, those of ordinary skill in the art will appreciate that other embodiments are also possible.

In the preferred embodiment, an active-server-page and applet-driven utility for plotting and automatically curve-fitting XY data using a polynomial best-fit regression technique are used. XY data may be displayed in a Web browser via a Java applet and an Active Server Page (ASP) extracted from the Excel spreadsheet. The raw data for plotting may be maintained in the Excel spreadsheet Workbook, located on the server. The user modifies this file at will and then plots the data using the applet executed remotely from the ASP. The data for plotting is read by the ASP and placed in the parameter tag fields of the applet. The ASP then executes a linear and quadratic least squares regression function, resulting in a curve-fit that is also supplied to the applet via parameter tags for plotting as an overlay on the raw data. The plot then appears in a standard Web window. The regression function creates a best-fit overlay curve based on either a linear or quadratic fit (best choice defined in the least-squares sense by the ASP from the raw data points).

In a further embodiment of the invention, an active-server-page and applet-driven utility may be used for plotting and automatically curve-fitting XY data using a minimum best-fit regression technique. XY plotting data in a raw ASCII form are preferably stored on a remote server in a conventional manner. These data can originate from a text file, a database, or a spreadsheet. For the purpose of this example, these data originate from a spreadsheet. The data, once stored, are retrieved by the GenericPlotter active server page function where they are processed to determine a generalized least squares best-fit function. This best fit function results in the production of coefficients of a regression equation that are used to produce an overlay of data illustrating the goodness of fit between the raw data and the newly-determined regression function. Together, both the raw plotting data and the regression data are written to an HTML page containing both a call to and parameter tags for use by an applet, which remains resident on a client machine. Upon writing these data to the HTML page, these data become fixed and resident within the HTML page of a client machine. The retrieval of the HTML page by the client machine is accomplished automatically by specifying the name of the active server page in the URL window associated with the name of the server's domain.

The client machine maintains as a plug-in a Java applet which is designed to read the parameter tags contained within the HTML page. The Java applet function retrieves the original ASCII data and the best-fit regression data contained within the parameter tags of the HTML form now resident on the client machine and reads these data into arrays within the applet class file. The applet class file processes these two data sets and creates within the browser window resident on the client's machine a two-dimensional plot containing both the raw data and an overlay of regression data. The plot itself, while resident on the client machine, is generated solely by the client, thereby obviating the need to pass an image file from server to client.

The system of the present invention differs from existing automatic plotting processes in several ways. The raw ASCII data are written directly from the server to the client. No image or plot is written from server to client. The client is fully responsible for generating the actual plot via the plotting functions contained within the applet. This is highly advantageous where transmission bandwidth is limited. Also, HTTP tunneling is advantageously not required, which identifies the server machine with which the client machine must be associated. In this way, the client machine is not tied physically to one server. Rather, any server containing the active server page that generates the applet call is sufficient to supply the data for the client machine. applet Java Security policies are advantageously not altered or breached in the process of reading the data from the server because the applet within the client is reading fixed values directly from the parameter tags contained within the applet call in the HTML page.

In operation, the execution takes place on both the server and the client. A Raw ASCII data file containing the data to be plotted either exists or is created by an external process or an individual. In the current embodiment, this file is read by Excel and is placed in a table, which is then saved under a specific name ("rawData.xls", in this example). The relationship between this aspect of the invention and the previous is that the raw ASCII data created by the ReadBMP utility already provide the data in the form necessary for direct access by the ASP. Once stored, an active server page reads this file and places the data in the appropriate format for calling within the resulting HTML page to be displayed on the client. Meanwhile, on the client, the sending of the HTML to the client's browser triggers the retrieval of the applet on the client, now executing in the client browser. The applet retrieves the parameters written to the HTML page on the client and displays a plot within the browser window, together using linear least squares which renders the best-fit curve to be overlaid on the raw data in addition to the governing best-fit equation.

The process of causing an ASP to read an MS Excel named data range is described in the open literature, so the exact steps will be omitted from this embodiment. However, this named range enables an Active Server Page (ASP) to read directly from the MS Excel file using the handle provided by the named range specified in the Figure. The named range is employed by the Open Database Connectivity (ODBC) manager to link the contents of the MS Excel file to the ADO (ActiveX Data Objects) used within the ASP so that the contents of the MS Excel file can be read automatically. The following steps describe the process of setting up the Excel spreadsheet. The steps begin with the assumption that the spreadsheet has been open. Steps 1 through 3 below detail the creation of a named range of cells within the Excel spreadsheet.

1) Enter data in (x,y) format: one value per cell. The first row of the worksheet must be the name of the x and y data columns, respectively 2) Create a name for the range of cells from which the Web page will retrieve the data. Click and drag the mouse across the cells to include within the range.

3) Select Insert→Name→Define→ Enter the name of the selected region in the worksheet. Name of selected region below is "dataFields" (where "dataFields" represents an example name for the range used to illustrate the functioning of the APU within the embodiment).

Once the spreadsheet has been created and a selected range of cells has been defined, it is necessary to make the spreadsheet range accessible as a ActiveX Data Object (ADO). This procedure will permit the active server page to open and retrieve the data within the Excel spreadsheet. This is begun by selecting "database administration," found by going to the Start button and proceeding as follows: Settings→Control Panel→Administrative Tools→Data Sources (ODBC). Double-clicking on the Data Sources (ODBC) icon will bring up the window shown in FIG. 4. Be sure to click on the System DSN (Data Source Name) tab.

Clicking on the Add button adds a new data source to the System Data Source area. Select "Microsoft Excel Driver (*.xls)" and click on Finish. The Data Source Name ("rawData" in this case) is then added. Then, Workbook is selected. Pressing Select Workbook will create a navigation window. The user must then navigate to the specific Excel file located on the system's storage drive, select the file, and close out the ODBC Administrator tool. Once completed, this permanently links the specified Excel spreadsheet, named range, and workbook to an ADO which is then accessible within the body of the ASP code.

The applet is the plotting engine. It receives as parameters the raw data read by the active server page from the Excel file via the ADO interface and converts those raw data points into a plot, displayed in the Web browser window. The applet reads the data into character string arrays and then converts them to floating point values. The data are then evaluated to determine maximum and minimum X and Y coordinate limits. Axes are drawn in the Web Browser window, and the data points are converted into (X,Y) pairs scaled to the size of the axes. The paint method uses a drawLine( ) function to convert each (X,Y) pair into a line segment between the current and next set of data points read in. Two plots are drawn: the raw data and the best-fit function (determined using least squares within the active server page). Both are input via a parameter array within the applet.

A preferred embodiment of the applet is discussed below to identify key features of the applet and raise their importance to the attention of the reader. Data are read by the applet through parameters passed in via the active server page into arrays. These arrays are initially filled as text strings and then translated into floating point values. Two sets of floating point arrays are created: one set for the raw and another set for the best-fit model data. A SloadData[ ] string and the SloadModel[ ] string are used to read in the data from the applet parameter list. These strings feature both the X and Y data. These data are then transformed into floating point values and stored in a Data[ ] and Model[ ] arrays, respectively. The X and Y components are then separated and stored in an xData[ ], yData[ ], xModel[ ], and yModel[ ] arrays. The size of these arrays is arbitrarily set to 1500 elements (implies 3000 raw data values and 3000 best-fit values). Those of ordinary skill in the art will appreciate that by using vectors, it would be possible to dynamically dimension these arrays to be as large or small as required by the quantity of data contained in the applet parameter list. Other embodiments of this method for other applications have employed the use of vectors. It is important to note that the present embodiment does not represent the most efficient implementation of the language constructs. Development efforts focused on improving operational efficiency can no doubt increase the performance and reduce memory consumption of the methods. It is important to note, however, that in specialized circumstances in which operation is limited by physical memory and the characteristic sizes of data are known in advance, specifying these as fixed quantities frequently represents the most efficient embodiment.

The data are read in a usePageParams( ) method via the following two lines of code: SloadData=getparameter ("loadData"); and loadModel=getparameter("loadModel"). An extractData( ) method is then used to translate from text to numerical values. First, the length of the data array must be determined. Next, it is necessary to loop through this array using an index variable to determine whether the end of the string has been reached. Instances of commas (",") are used as delimiters in the applet parameter list. Whenever one is found, the program knows that it has reached the end of another data value. Now, the Data[ ] array is filled with all of the data elements, commas removed, and the data are separated into X and Y components. The same steps as above are then performed for the model data.

Once the data are read, they need to be scaled and drawn in a grid. The grid area is drawn using a drawGrid( ) method, which also measures ticks by the quantity specified in the applet parameter list. The method also draws the numerical values next to the axis major tick marks. Presently, the selection of minimum and maximum values in the X and Y coordinate directions are based on the minimum and maximum of the raw data and model data (whichever are smallest and largest, respectively). The values of both the raw data and the model are compared with the local minima and maxima, and if smaller or larger, are assigned to the new values of the local minima and maxima, ultimately becoming the global minima and maxima, respectively.

The data scaling and plotting are accomplished in the example in one step. First, the scale factors for the X and Y component directions are defined with respect to the size of the browser plotting window and the range of the maximum and minimum values in the X and Y component directions. Next, these scale factors are applied to each data point inside of a FOR loop that draws a spline between the current value of the data points and their next value. The same method is then applied to scaling the model data as was applied to the raw data above.

Figure 19:
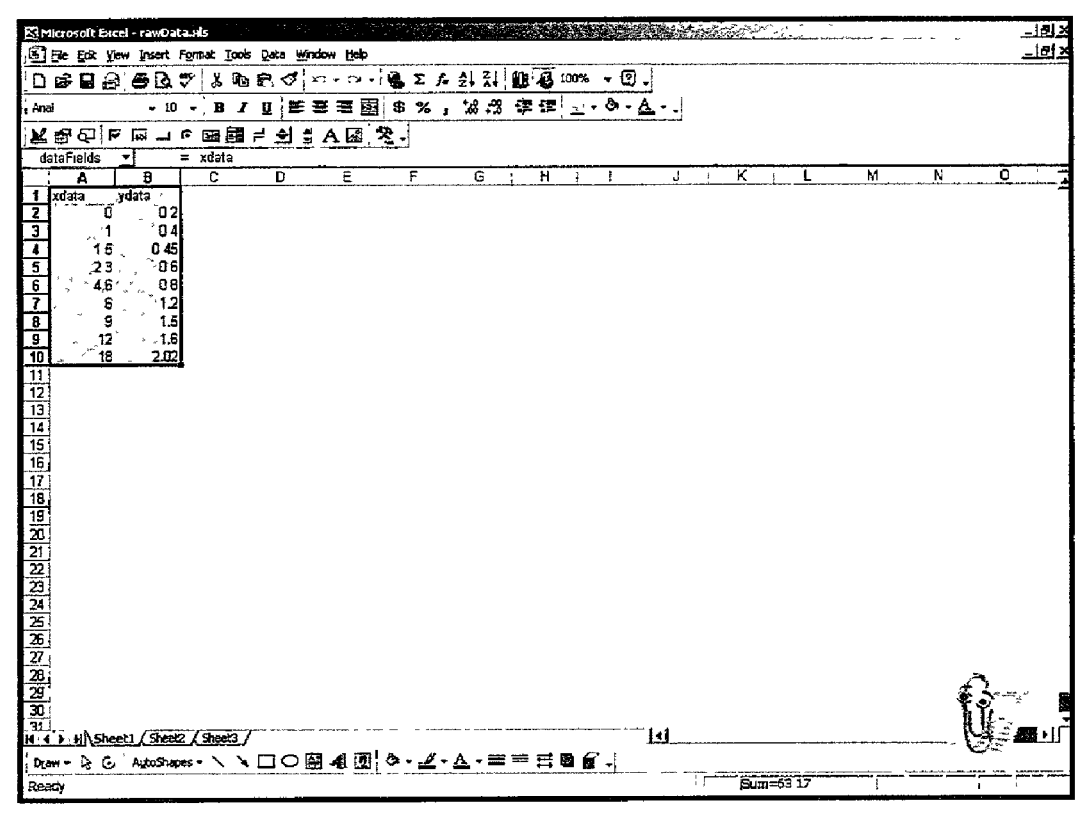

The active server page in this example is written in VBScript. However, those of ordinary skill in the art will appreciate that the page could also be written in other languages, such as JavaScript. Either scripting language can be employed and will achieve identical results, depending on the preference of the developer. VB Script is frequently employed by those developing ASP (often the native language used within the MS Visual Studio development environment).The first step involved is opening the ADO object for read access. The fields defined within the named range "dataFields" are selected from the Excel spreadsheet. FIG. 19 illustrates a sample input file containing (x,y) data points associated with the "dataFields" named range. This file will be used to illustrate the plotting utility later in FIGS. 20 and 21.

The ADO connection is then opened for reading. The data elements are read into arrays. Then, the file is read using a WHILE loop, which reads to the end of the named range. The applet itself is called within the BODY text segment of the code. The data just read is written as parameters within the scope of the applet.

In this example, the raw data and the model data are both written as parameters from the active server page. Thus, the applet is loaded on the client and receives its data from the HTML page written as a result of the execution of the active server page. In this way, only ASCII text is passed from the server to the client, as opposed to server-based plotters, in which JPEG or GIF data are written to the client. This provides the significant advantage when there is a concern over client-server bandwidth, as only text-based data is passed between the two, and the quantity of text-based data is relatively small (that is, representative of fewer than several hundred data points).

The model data is created using a subroutine, cFitLine( ), that finds a least-squares linear or quadratic solution for the data. The selection of linear or quadratic model is made on the basis of a weighted distance parameter ("lineChiSquare", "quadChiSquare") which compares the distance between each raw data point and the best-fit model equation based on $y=mx+b$ (linear) or $y=c1+c2x+c3x^2$. The model (linear, quadratic) is selected by determining the weighted distance measure from the linear model with the quadratic model. The smaller of the two distance measures results in the winning model. The regression data is preferably written as an overlay on top of the raw data; and optional variance and standard deviation can also be written, together with a chi-square fit parameter indicating the degree to which the regression curve matches the raw data.

The active server page automatically determines the best form of the least squares regression curve using a chi-squared best fit (Mahalanobis Distance) comparator function, and fills the applet parameter tag fields within the HTML page with the data associated with both the raw data read from the spreadsheet and the least squares regression curve. These numeric values are written to the HTML page in the form of a list of ASCII values. This list of ASCII values associated with the raw data and the regression curve overlay are read by the applet on the client machine as arrays of floating point numbers. The arrays of floating point numbers are automatically scaled by the applet and are plotted within the HTML window on the client machine.

Figure 20:
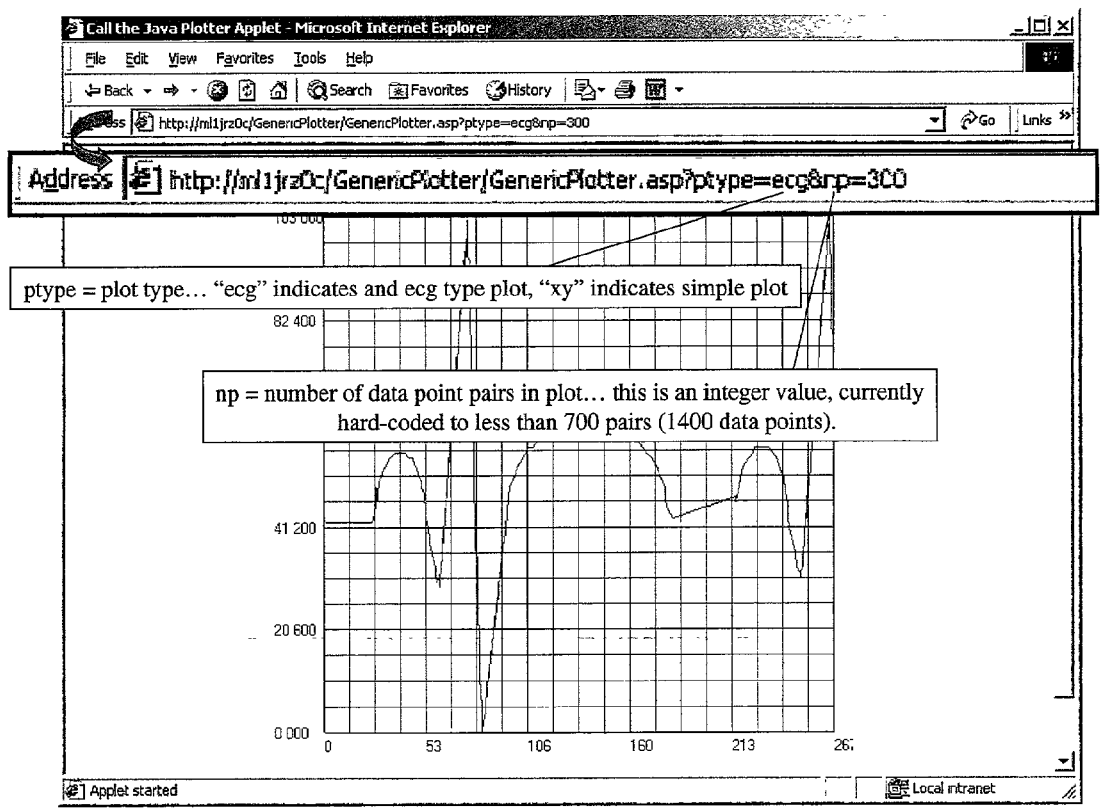
FIG. 20 is a computer screen shot illustrating the execution of the APU, with emphasis on the parameters contained within the URL call to the utility.

The APU method provides the capability to select the type of plot to be created on the client by specifying within the URL parameter list a choice of plot type and the quantity of data points to be plotted. One of the benefits of the APU method is in its ability to plot both the ECG or EEG data directly extracted by the ReadBMP VB Script utility, the C++, or Java equivalent. FIG. 20 is a computer screen shot illustrating the execution of the APU, with emphasis on the parameters contained within the URL call to the utility. The parameter list requests the plot type and the number of data points contained within the plot. A plot type of "ecg" indicates an ECG plot. A plot type of "xy" indicates a simple graph. FIG. 20 illustrates how the GenericPlotter.asp page can be used to select the type of plot and the quantity of data points specified to be plotted by the client. The URL address bar in the instance of FIG. 20 reads as follows:

http://ml1jrz0c/GenericPlotter.asp?ptype=ecg&np=300

The ASP page receives two parameters: ptype, which is used to specify whether the type of plot to be generated is an ECG trace, and the number of data point pairings (here, np=300 corresponds to the quantity of (x,y) pairs). Selecting ptype=ecg turns off the curve-fitting capability in the current embodiment and enables the plotting of the single set of raw data on the client. An example implementation of this was shown in FIG. 11.

Specifying the following in the URL causes a standard {x,y} plot to be generated, with curve-fitting enabled. Thus, to plot the data of FIG. 19, the following URL would be invoked:

http://ml1jrz0c/GenericPlotter.asp?ptype=xy&np=9

Figure 21:
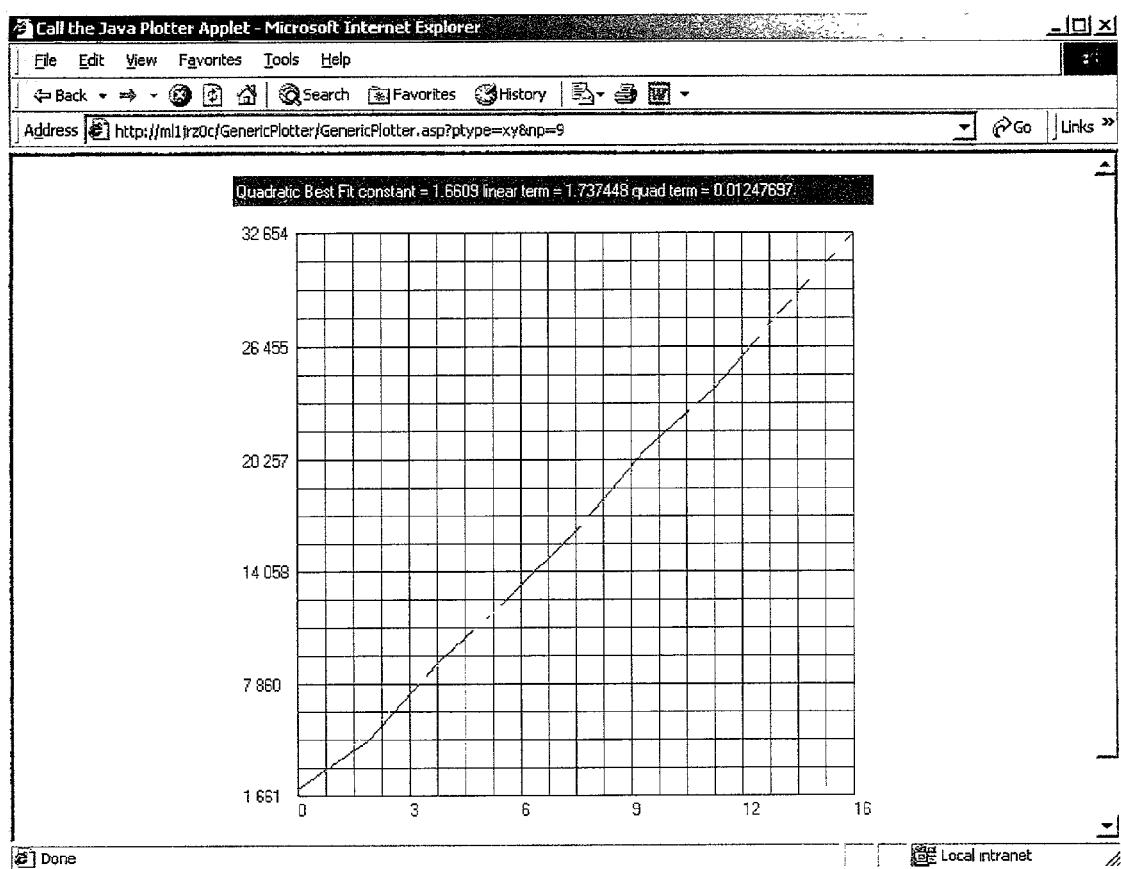
FIG. 21 is a computer screen shot of the "x-y" plotting output of the applet-based APU used in the present invention.

Specifying ptype=xy and np=9 tells the ASP page that a standard {x,y} plot is to be generated, and to plot the first 9 data points. Thus, a curve-fit will also be generated and sent to the client. The result of this action is demonstrated in the screen shot of FIG. 21. FIG. 21 shows the raw data plot with the best-fit overlay of the data, and the best-fit equation. When "xy" plotting is selected, a curve-fitting routine is automatically invoked by the ASP that generates a least-squares fit of the plot data which is overlaid on the original plot. In this example, 9 data points are selected for plotting, from the file depicted in FIG. 19.

The present invention has significant benefits over the prior art. Access to the ASCII form of the data through a Web interface enables overlaying analytical tools either through methods written in the ASP code or through external .dll files that promote, for example, the ability to perform signal analysis (e.g., frequency analysis, signal segment length (ST segment) analysis, averaging of the signal, etc.). This may be accomplished through the use of macros contained within the Excel spreadsheet tool itself (that is, Visual Basic macros to support Fourier Transforms, Power Spectral Analysis, Lomb Periodogram and Wavelet analysis, for instance). Alternatively, these methods can be written in Visual Basic or Jscript (or other languages) that can perform this analysis on the raw data inside of the server application. The results can be posted to any Web-enabled device (Personal Digital Assistant, Laptop, Cell Phone).

Because the present invention provides access to the ASCII values of the pixels, it is not necessary to paste the entire bitmap image on the screen. A partial image may be provided on the screen (or segments of an image) without having to pass the rawjpg or .bmp image from the server to the Web client. The present invention passes ASCII data between the server and the client, which enhances overall performance. Also, because the methods are written in Visual Basic, they can be instantiated as back-end methods inside of already-existing products.

Mathematical processing of regression curve and extraction of raw data occurs on the server machine (not the client), thereby satisfying security restriction associated with the (standard) inability of applets to access data files on a local machine (that is, without disabling special security restrictions on the applet). The present invention ensures that data can be plotted on any machine that can support a Web Browser and a Java Plug-in. Processing on the server and transmission of ASCII data via HTML to client provides a solution for low-bandwidth communications between any server and client since plot is generated on the client, using the client's processor.

Although this invention has been described with reference to particular embodiments, it will be appreciated that many variations may be resorted to without departing from the spirit and scope of this invention as set forth in the appended claims. For example, the embodiments disclosed herein incorporate a single application server, while one of ordinary skill in the art will appreciate that any number of computer system application servers, data servers, and Web servers may achieve the invention. Similarly, in addition to the a separate image reader, data object, signal processor, and imaging object illustrated herein, the software of the present invention can comprise a single application having individual components or a suite of applications, and its form is not particularly limited.

What is claimed is:

1. A method for automatically converting a graphical trace of acquired patient data into digital data suitable for digital signal processing, comprising the steps of:
   receiving a first file comprising data representative of an image including said graphical trace of acquired patient data;
   analyzing said received data to identify individual pixels comprising said graphical trace in said image representative data;
   automatically generating a second file, different to said first file, comprising graphical trace representative data including a plurality of pixel representative data elements in a desired data format identifying the relative location of said individual pixels in relation to a reference point;
   generating said desired data format by identifying the relative location of said individual pixels and identifying at least one of, (a) color of said individual pixels and (b) luminance amplitude of said individual pixels; and
   storing said generated pixel representative data elements comprising said second file.

2. A method according to claim 1, including the step of scanning a paper reproduction of said graphical trace to provide said data representative of said image including said graphical trace.

3. A method according to claim 1, wherein said data representative of said image including said graphical trace is in at least one data format of, (a) a bitmap file format, (b) a graphical interchange format (GIF format), (c) a (Joint Photographic Expert Group) JPEG format and (d) a Tagged Image File Format (TIFF).

4. A method according to claim 1, wherein said desired data format is an ASCII format comprising:
   (x, y, color)i
   where (x) represents the x-coordinate position of the i-th pixel; (y) represents the y-coordinate position of the i-th pixel, and color represents the RGB color of the i-th pixel.

5. A method according to claim 1, wherein said graphical trace of a medical parameter comprises at least one of, (a) an electrocardiogram trace, (b) an electro-encephalogram trace and (c) a ventilator parameter trace comprising at least one selected from the group consisting of respiratory rate, tidal volume, minute volume, pulse oximetry, etc.), and (d) a blood parameter trace.

6. A method according to claim 1, further comprising the steps of:
   formatting said received data into a format compatible with a procedure located at a remote destination, said procedure being for processing said data representative of said graphical trace to provide processed data suitable for use in presenting said graphical trace in a displayed image; and
   communicating said formatted data to said remote destination in response to a user command; and
   generating said displayed image at said remote destination using said formatted data.

7. A method according to claim 1, further comprising the steps of:
   decoding said data format to provide formatted data in a decoded format incorporating data fields conveying said data representative of said graphical trace; and
   initiating execution of a procedure for accessing said data fields conveying said data representative of said graphical trace and exclusive of establishing customized security protocol settings enabling access by said procedure to said formatted data, said procedure processing said data representative of said graphical trace to provide processed data suitable for use in presenting said graphical trace in a displayed image.

8. A method for automatically converting a graphical trace into digital data suitable for digital signal processing, comprising the steps of:
   receiving a first file comprising data representative of an image including a graphical trace;
   analyzing said received data to identify individual pixels comprising said graphical trace in said image representative data;
   receiving user color selection information specifying a color;
   automatically generating a second file, different to said first file, comprising graphical trace representative data including a plurality of pixel representative data elements of pixels of said specified color in a desired data format identifying the relative location of said individual pixels in relation to a reference point; and
   storing said generated pixel representative data elements comprising said second file.

9. A method according to claim 8, wherein said storing step comprises storing said generated pixel representative data elements in a second file of format selected by a user from formats including, (a) a text file format, (b) a word file format, (c) a spreadsheet format and (d) a database compatible format.

10. A method according to claim 8, further comprising the steps of:
determining file size of said received first file from file header information; and
extracting pixel data for use in said generating step by performing a binary read of said first file of determined size.

11. A method according to claim 8, further comprising the steps of:
extracting raw binary data representing pixel data in three 8-bit segments per pixel;
comparing extracted pixel data against a user-specified desired colormap to selectively filter those pixels corresponding to those of a desired color; and
generating coordinates of the filtered extracted pixel data in a desired format for use in said step of generating a plurality of pixel representative data elements.

12. A method according to claim 8, further comprising the step of analyzing generated pixel representative data elements to determine frequency of features embodied in said graphical trace.

13. A method according to claim 8, further comprising the step of analyzing generated pixel representative data elements representing a segment of said graphical trace to determine frequency of features embodied in said graphical trace segment.

14. A method according to claim 8, wherein said graphical trace represents a medical parameter and including the step of automatically predicting changes in medical parameter frequency characteristics.

15. A method according to claim 14, wherein said graphical trace of a medical parameter comprises at least one of, (a) an electro-cardiogram trace, (b) an electro-encephalogram trace and (c) a ventilator parameter trace, and (d) a blood parameter trace.

16. A method according to claim 14, further comprising the step of automatically determining whether said predicted changes in medical parameter frequency characteristics are statistically significant for a specific patient.

17. A method according to claim 16, further comprising the step of determining whether said predicted changes in medical parameter frequency characteristics are statistically significant based on medical record information for said specific patient.

18. A method according to claim 8, further comprising the steps of:
formatting said received data representative of an image into a format compatible with a procedure located at a remote destination, said procedure being for processing said data representative of said graphical trace to provide processed data suitable for use in presenting said graphical trace in a displayed image; and
communicating said formatted data to said remote destination in response to a user command; and
generating said displayed image at said remote destination using said formatted data.

19. A method according to claim 8, further comprising the steps of:
decoding said data elements to provide formatted data in a decoded format incorporating data fields conveying said data representative of said graphical trace;
initiating execution of a procedure for accessing said data fields conveying said data representative of said graphical trace and exclusive of establishing customized security protocol settings enabling access by said procedure to said formatted data, said procedure processing said data representative of said graphical trace to provide processed data suitable for use in presenting said graphical trace in a displayed image.

20. A method for automatically converting a graphical trace of acquired patient data into digital data suitable for digital signal processing, comprising the steps of:
receiving data representative of an image including said graphical trace of acquired patient data;
automatically generating a second file, different to said first file, comprising formatted data representing graphical trace representative data including a plurality of pixel representative data elements in a desired data format compatible with a procedure located at a remote destination, said procedure being for processing said data representative of said graphical trace to provide processed data suitable for use in presenting said graphical trace in a displayed image;
communicating said formatted data to said remote destination in response to a user command; and
generating said displayed image at said remote destination using said formatted data.

21. A method for automatically converting a graphical trace of acquired patient data into digital data suitable for digital signal processing, comprising the steps of:
receiving a first file comprising data representative of an image including said graphical trace of acquired patient data;
automatically generating a second file comprising graphical trace representative formatted data including a plurality of pixel representative data elements incorporating data fields conveying said data representative of said graphical trace;
initiating execution of a procedure for accessing said data fields conveying said data representative of said graphical trace and exclusive of establishing customized security protocol settings enabling access by said procedure to said formatted data, said procedure processing said data representative of said graphical trace to provide processed data suitable for use in presenting said graphical trace in a displayed image.

22. A method according to claim 20, wherein said generating step comprises formatting said received data representative of an image into tagged fields in an HTML Active Server Page format.

23. A method according to claim 20, wherein said format compatible with a procedure located at a remote destination comprises one or more selected from the group consisting of (a) a bitmap file format, (b) a graphical interchange format (GIF format), (c) a (Joint Photographic Expert Group) JPEG format, and (d) a Tagged Image File Format (TIFF).

24. A method according to claim 20, wherein said procedure located at a remote destination for processing said data representative of a graphical trace is a Java applet.

25. A system for automatically converting a graphical trace of acquired patient data into digital data suitable for digital signal processing, comprising:
an image reader programmed to:
(1) receive a first file comprising data representative of an image including said graphical trace of acquired patient data;
(2) analyze said received data to identify individual pixels comprising said graphical trace in said image representative data;
(3) automatically generate a second file comprising graphical trace representative data including a plurality of pixel representative data elements in a desired data format identifying the relative location of said individual pixels in relation to a reference point;

(4) generating said desired data format by identifying the relative location of said individual pixels and identifying at least one of, (a) color of said individual pixels and (b) luminance amplitude of said individual pixels; and a data object programmed to store said generated pixel representative data elements comprising said second file.

26. The system of claim 25, wherein said data representative of said image including said graphical trace is in at least one data format of, (a) a bitmap file format, (b) a graphical interchange format (GIF format) (c) a (Joint Photographic Expert Group) JPEG format and (d) a Tagged Image File Format (TIFF).

27. The system of claim 25, wherein said desired data format is an ASCII format comprising:

(x,y, color)i where (x) represents the x-coordinate position of the i-th pixel; (y) represents the y-coordinate position of the i-th pixel, and color represents the RGB color of the i-th pixel.

28. The system of claim 27, wherein said graphical trace of a medical parameter comprises at least one of, (a) an electro-cardiogram trace, (b) an electro-encephalogram trace and (c) a ventilator parameter trace, and (d) a blood parameter trace.

29. The system of claim 25, further comprising:

a signal processor programmed to format said received data representative of an image into formatted data compatible with a procedure located at a remote destination, said procedure being for processing said data representative of said graphical trace to provide processed data suitable for use in presenting said graphical trace in a displayed image; and an imaging object programmed to communicate said formatted data to said remote destination in response to a user command to generate said displayed image at said remote destination using said formatted data.

30. The system of claim 25, further comprising:

a signal processor programmed to decode said data format to provide formatted data in a decoded format incorporating data fields conveying said data representative of said graphical trace; and an imaging object programmed to initiate execution of a procedure for accessing said data fields conveying said data representative of said graphical trace and exclusive of establishing customized security protocol settings enabling access by said procedure to said formatted data, said procedure processing said data representative of said graphical trace to provide processed data suitable for use in presenting said graphical trace in a displayed image.

31. A system for automatically convening a graphical trace into digital data suitable for digital signal processing, comprising:

an image reader programmed to:

(1) receive a first file comprising data representative of an image including a graphical trace;

(2) analyze said received data to identify individual pixels comprising said graphical trace in said image representative data;

(3) receive user color selection information specifying a color;

(4) automatically generate a second file comprising graphical trace representative data including a plurality of pixel representative data elements of pixels of said specified color in a desired data format identifying the relative location of said individual pixels in relation to a reference point; and a data object programmed to store said generated pixel representative data elements comprising said second file.

32. The system of claim 31, wherein said data object is programmed to store said generated pixel representative data elements in a second file of format selected by a user from formats including, (a) a text file format, (b) a word file format, (c) a spreadsheet format and (d) a database compatible format.

33. The system of claim 31, wherein said image reader is further programmed to determine file size of said received data representative of an image from file header information and to extract pixel data for use in said generating step by performing a binary read of said file of determined size.

34. The system of claim 31, wherein said image reader is further programmed to extract raw binary data representing pixel data in three 8-bit segments per pixel; compare extracted pixel data against a user-specified desired color map to selectively filter those pixels corresponding to those of a desired color; and generate coordinates of the filtered extracted pixel data in a desired format for use in generating a plurality of pixel representative data elements.

35. The system of claim 31, wherein said image reader is further programmed to analyze generated pixel representative data elements to determine frequency of features embodied in said graphical trace.

36. The system of claim 31, wherein said image reader is further programmed to analyze generated pixel representative data elements representing a segment of said graphical truce to determine frequency of features embodied in said graphical trace segment.

37. The system of claim 31, wherein said graphical trace represents a medical parameter and including the step of predicting changes in medical parameter frequency characteristics.

38. The system of claim 37, wherein said graphical trace of a medical parameter comprises at least one of, (a) an electrocardiogram trace, (b) an electro-encephalogram trace and (c) a ventilator parameter trace, and (d) a blood parameter trace.

39. The system of claim 37, wherein said image reader is further programmed to determine whether said predicted changes in medical parameter frequency characteristics are statistically significant for a specific patient.

40. The system of claim 39, wherein said image reader is further programmed to determine whether said predicted changes in medical parameter frequency characteristics are statistically significant based on medical record information for said specific patient.

41. The system of claim 31, further comprising:

a signal processor programmed to format said received data representative of an image into formatted data compatible with a procedure located at a remote destination, said procedure being for processing said data representative of said graphical trace to provide processed data suitable for use in presenting said graphical trace in a displayed image; and an imaging object programmed to communicate said formatted data to said remote destination in response to a user command to generate said displayed image at said remote destination using said formatted data.

42. The system of claim 31, further comprising:

a signal processor programmed to decode said data elements to provide formatted data in a decoded format incorporating data fields conveying said data representative of said graphical trace; and an imaging object programmed to initiate execution of a procedure for accessing said data fields conveying said data representative of said graphical trace and exclusive of establishing customized security protocol settings enabling access by said procedure to said formatted data, said procedure processing said data representative of said graphical trace to provide processed data suitable for use in presenting said graphical trace in a displayed image.

43. A system for automatically converting a graphical trace of acquired patient data into digital data suitable for digital signal processing comprising:

an image processor programmed to receive a first file comprising data representative of an image including said graphical trace of acquired patient data and automatically generate a second file comprising graphical trace representative formatted data including a plurality of pixel representative data elements in a desired data format compatible with a procedure located at a remote destination, said procedure being for processing said data representative of said graphical trace to provide processed data suitable for use in presenting said graphical trace in a displayed image; and an imaging object programmed to communicate said formatted data to said remote destination in response to a user command to generate said displayed image at said remote destination using said formatted data.

44. A system for automatically converting a graphical trace of acquired patient data into digital data suitable for digital signal processing comprising:

an image processor programmed to receive a first file comprising data representative of an image including said graphical trace of acquired patient data and automatically generate a second file comprising graphical trace representative formatted data including a plurality of pixel representative data elements incorporating data fields conveying said data representative of said graphical trace; and an imaging object programmed to initiate execution of a procedure for accessing said data fields conveying said data representative of said graphical trace and exclusive of establishing customized security protocol settings enabling access by said procedure to said formatted data, said procedure processing said data representative of said graphical trace to provide processed data suitable for use in presenting said graphical trace in a displayed image.

45. The system of claim 43, wherein said image reader is further programmed to format said received data into tagged fields in an HTML Active Server Page format.

46. The system of claim 43, wherein said format compatible with a procedure located at a remote destination comprises one or more selected train the group consisting of (a) a bitmap file format, (b) a graphical interchange format (GIF format), (c) a (Joint Photographic Expert Group) JPEG format, and (d) a Tagged Image File Format (TIFF).

47. The system of claim 43, wherein said procedure located at a remote destination for processing said data representative of a graphical trace is a Java applet.

48. The system of claim 43, wherein said image processor and said imaging object are computer program components.

* * * * *